(12) United States Patent
Everland et al.

(10) Patent No.: US 8,877,246 B2
(45) Date of Patent: Nov. 4, 2014

(54) COMPOSITIONS AND METHODS FOR AUGMENTATION AND REGENERATION OF LIVING TISSUE IN A SUBJECT

(71) Applicant: Colopast A/S, Humlebaek (DK)

(72) Inventors: Hanne Everland, Bagsvaerd (DK); Peter Samuelsen, Rungsted Kyst (DK); Jakob Vange, Helsingoer (DK); Christian Clausen, Fredensborg (DE); Monica Ramos Gallego, Copenhagen SV (DK)

(73) Assignee: Coloplast A/S, Humlebaek (DK)

(*) Notice: Subject to any disclaimer, the term of this patent is extended or adjusted under 35 U.S.C. 154(b) by 0 days.

(21) Appl. No.: 13/739,020

(22) Filed: Jan. 11, 2013

(65) Prior Publication Data
US 2013/0251758 A1 Sep. 26, 2013

Related U.S. Application Data

(62) Division of application No. 12/735,976, filed as application No. PCT/EP2009/052431 on Mar. 2, 2009, now abandoned.

(30) Foreign Application Priority Data

Feb. 29, 2008 (DK) ................................ 2008 00307

(51) Int. Cl.
*A61K 9/00* (2006.01)
*A61K 9/14* (2006.01)
*A01N 63/00* (2006.01)
*A01N 65/00* (2009.01)
*A61L 27/36* (2006.01)
*A61L 27/18* (2006.01)
*A61L 27/38* (2006.01)
*A61L 27/56* (2006.01)

(52) U.S. Cl.
CPC ............. *A61L 27/3604* (2013.01); *A61L 27/18* (2013.01); *A61L 27/38* (2013.01); *A61L 27/56* (2013.01); *A61L 2400/06* (2013.01)
USPC ........... 424/489; 424/400; 424/500; 424/501; 424/93.7

(58) Field of Classification Search
CPC . A61L 2400/06; A61L 27/3604; A61L 27/38; A61L 27/56; A61K 9/14; A61K 9/146; A61K 9/205; A61K 9/5161
USPC .......................... 424/400, 489, 500, 501, 93.7
See application file for complete search history.

(56) References Cited

U.S. PATENT DOCUMENTS

| | | | |
|---|---|---|---|
| 4,822,741 A | 4/1989 | Banes | |
| 5,019,400 A | 5/1991 | Gombotz et al. | |
| 5,102,983 A | 4/1992 | Kennedy | |
| 5,759,190 A | 6/1998 | Vibe-Hansen et al. | |
| 5,989,269 A | 11/1999 | Vibe-Hansen et al. | |
| 5,989,463 A | 11/1999 | Tracy et al. | |
| 6,120,514 A | 9/2000 | Vibe-Hansen et al. | |
| 6,283,980 B1 | 9/2001 | Vibe-Hansen et al. | |
| 6,340,592 B1 | 1/2002 | Stringer | |
| 6,379,367 B1 | 4/2002 | Vibe-Hansen et al. | |
| 6,455,074 B1 | 9/2002 | Tracy et al. | |
| 6,495,152 B2 | 12/2002 | Steinbuchel et al. | |
| 6,558,664 B1 | 5/2003 | Stringer | |
| 6,592,598 B2 | 7/2003 | Vibe-Hansen et al. | |
| 6,592,599 B2 | 7/2003 | Vibe-Hansen et al. | |
| 6,599,300 B2 | 7/2003 | Vibe-Hansen et al. | |
| 6,599,301 B2 | 7/2003 | Vibe-Hansen et al. | |
| 6,676,969 B2 | 1/2004 | Geistlich et al. | |
| 6,841,151 B2 | 1/2005 | Stringer | |
| 2002/0094754 A1 | 7/2002 | Stringer | |
| 2003/0064511 A1 | 4/2003 | Stringer | |
| 2005/0129673 A1 | 6/2005 | Stringer | |
| 2006/0040894 A1* | 2/2006 | Hunter et al. | .................. 514/54 |
| 2006/0148077 A1 | 7/2006 | Thies | |
| 2006/0280726 A1* | 12/2006 | Chancellor et al. | .......... 424/93.7 |

FOREIGN PATENT DOCUMENTS

| | | |
|---|---|---|
| WO | WO 96/02209 | 2/1996 |
| WO | WO 98/08469 | 3/1998 |
| WO | WO 02/061052 | 8/2002 |
| WO | WO 02/083878 | 10/2002 |
| WO | WO 03/028545 | 4/2003 |
| WO | WO 2004/110512 | 12/2004 |
| WO | 2007028169 | 3/2007 |
| WO | WO 2007/028169 | 3/2007 |
| WO | WO 2007/101443 | 9/2007 |
| WO | 2008157059 | 12/2008 |

OTHER PUBLICATIONS

Kang et al. "The use of poly(lactic-co-glycolic acid) microspheres as injectable cell carriers . . . " J. Biomater, Sci., Polymer, vol. 17, No. 8, p. 925-939, Jan. 2005.
Newman et al. "Poly-d,l lactic-co-glycolic acid) microspheres as biodegradable microcarriers . . . " Elsevier, Biomaterials, vol. 25, No. 26, p. 5763-5771, Nov. 2004.
Xu et al. "Soft, porous poly(d, l lactide-do-glycotide) microcarriers designed for ex vivo studies . . . " Academy of Sci., vol. 944, No. 26, p. 144-159, Jan. 2001.
Schneiders et al. "Controlled release of gentamicin from calcium phosphate . . . " Elsevier, Biomaterials, vol. 27, No. 23, p. 4239-4249, Aug. 2006.
Gaffney et al. "The international and "NIH" units for thrombin-how do they compare?" Thrombosis and Haemostasis, vol. 74, No. 3, p. 900-903, Sep. 1995.
Mikos et al. "Preparation and characterization of poly(l-lactic acid) foams" Polymer, vol. 35, No. 5, p. 1068-1077, 1994.

* cited by examiner

*Primary Examiner* — Abigail Fisher
(74) *Attorney, Agent, or Firm* — Coloplast Corp., Coloplast A/S; Nick Baumann

(57) ABSTRACT

The present invention provides for a composition, for augmentation and regeneration of living tissue in a subject, comprising a population of porous microparticles of a biodegradable polymer, one or more mammalian cell populations, and optionally, a biocompatible adhesive.

18 Claims, 27 Drawing Sheets

FIG. 1A                    FIG. 1B

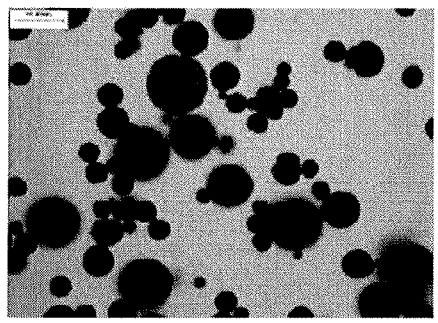 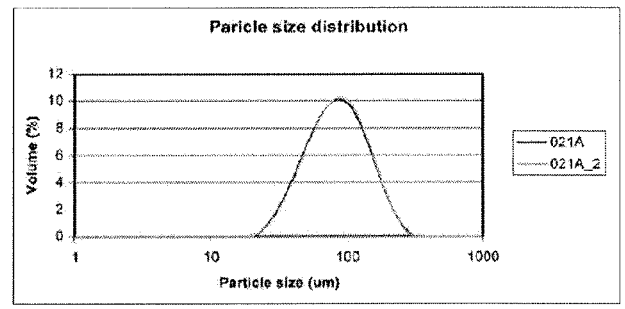
FIG. 3A	FIG. 3B
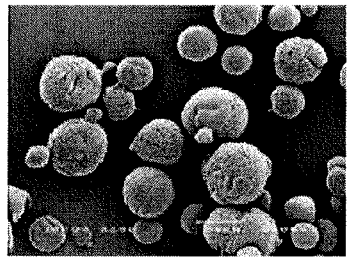 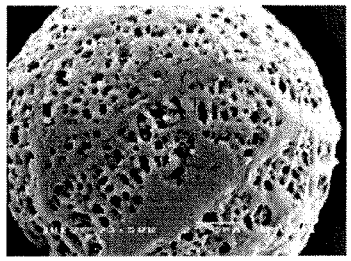 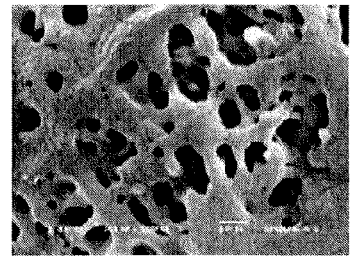
FIG. 3C	FIG. 3D	FIG. 3E
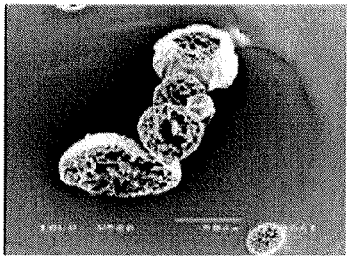 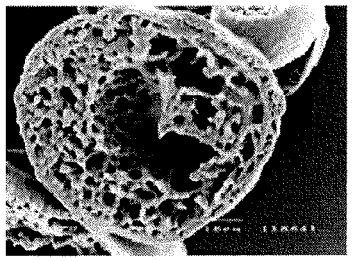 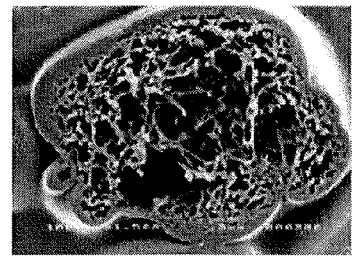
FIG. 3F	FIG. 3G	FIG. 3H
 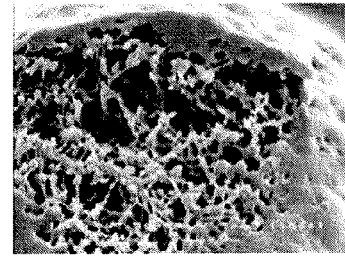
FIG. 3I	FIG. 3J

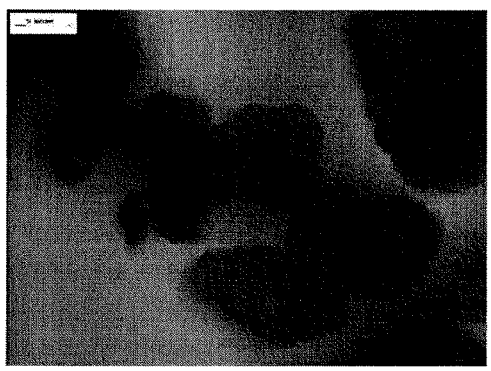
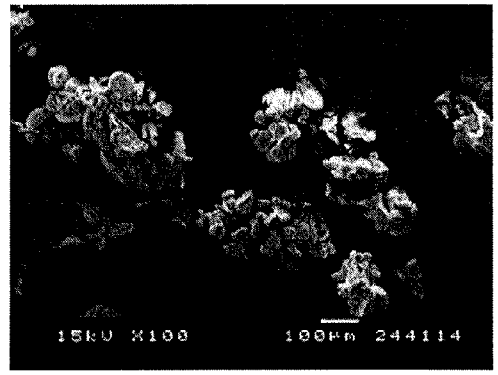
FIG. 4A  FIG. 4B
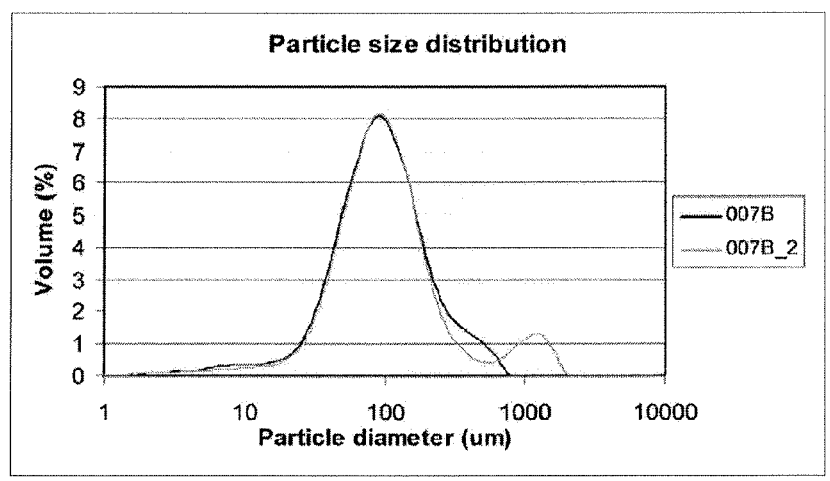
FIG. 4C

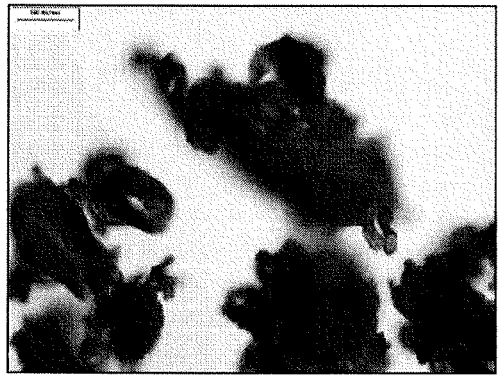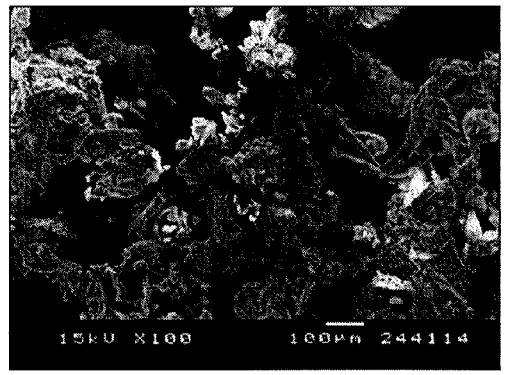
FIG. 5A  FIG. 5B
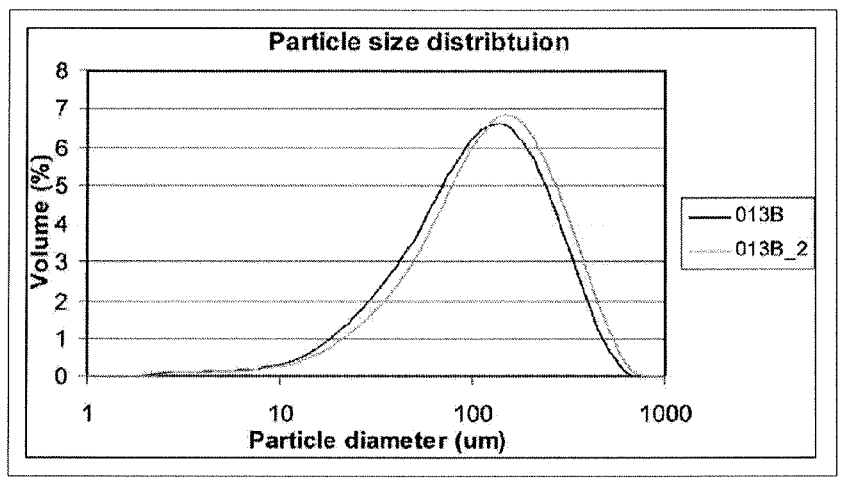
FIG. 5C

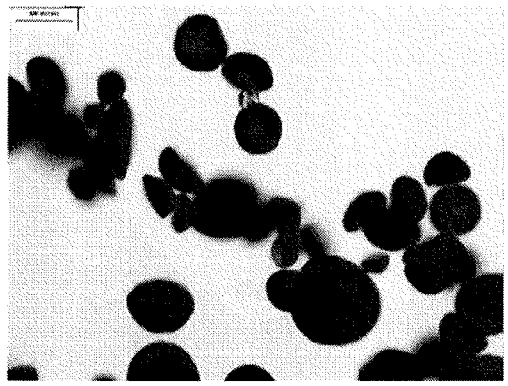
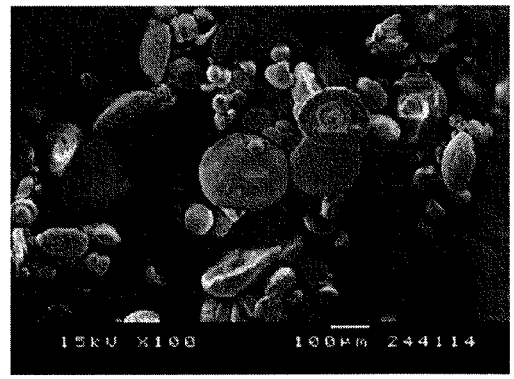
FIG. 6A  FIG. 6B
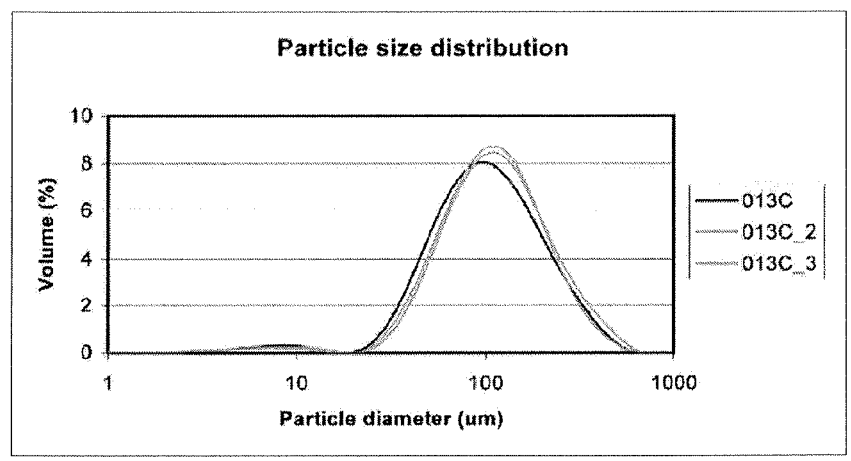
FIG. 6C

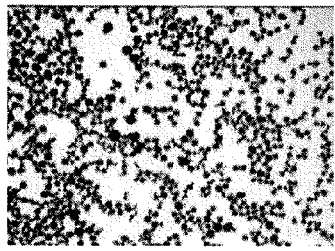 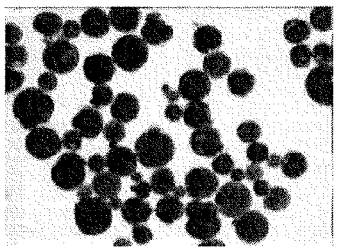 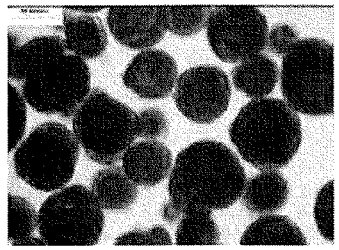
FIG. 11A  FIG. 11B  FIG. 11C
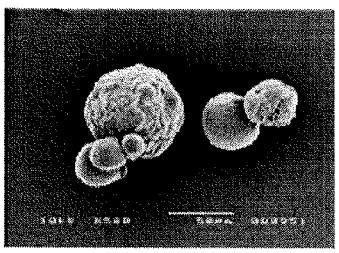 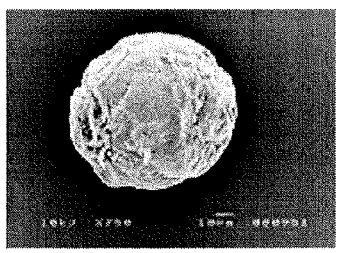 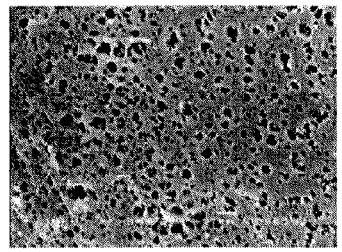
FIG. 11D  FIG. 11E  FIG. 11F
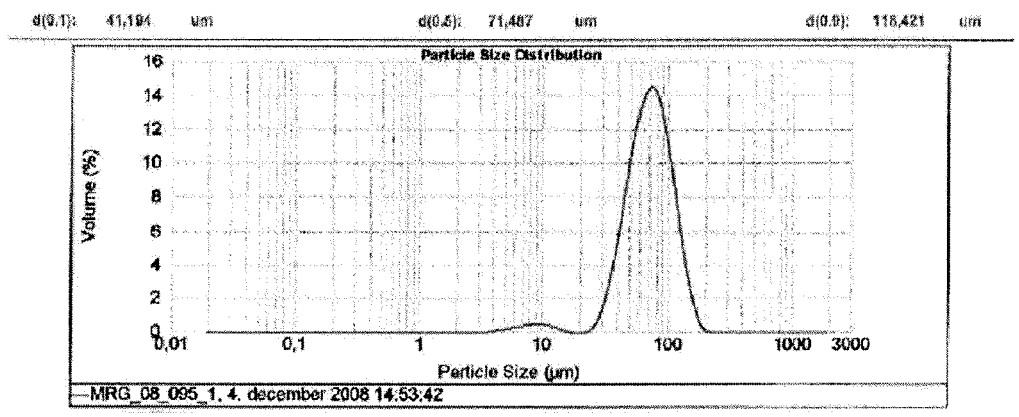
FIG. 11G

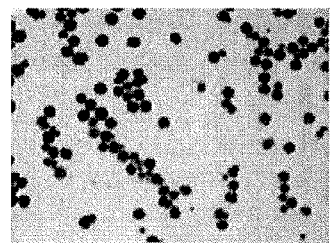 
FIG. 13A    FIG. 13B
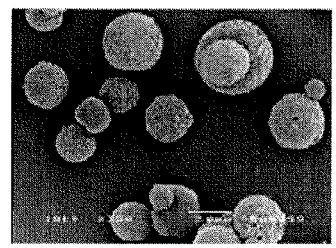 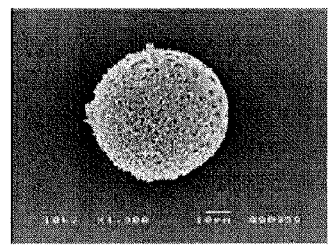 
FIG. 13C    FIG. 13D    FIG. 13E
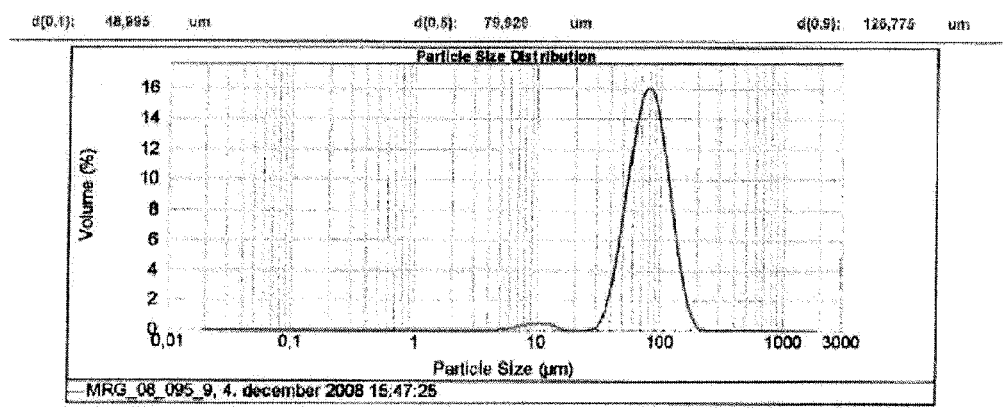
FIG. 13F

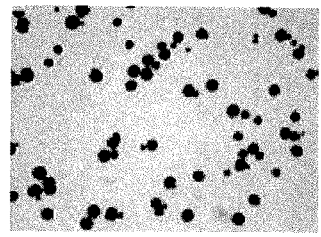
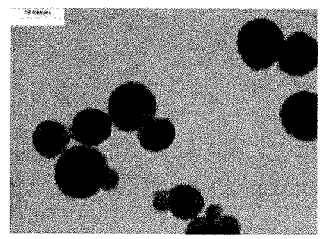
FIG. 14A  FIG. 14B
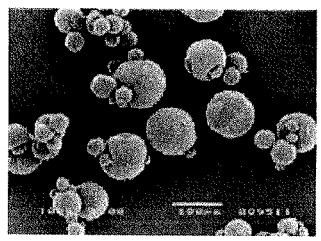
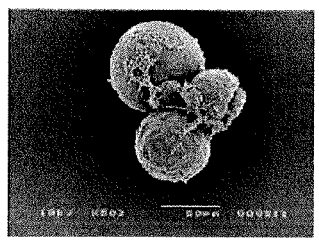
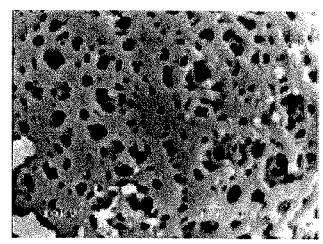
FIG. 14C  FIG. 14D  FIG. 14E
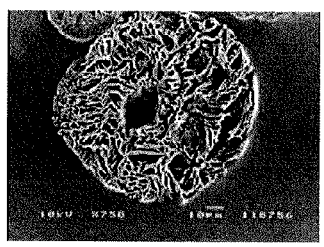
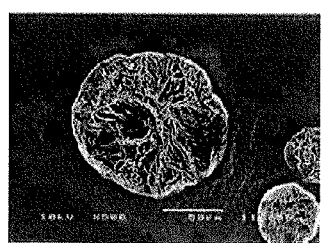
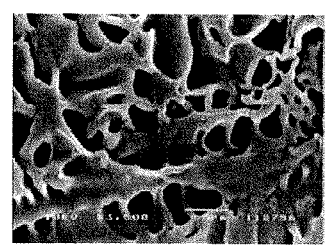
FIG. 14F  FIG. 14G  FIG. 14H

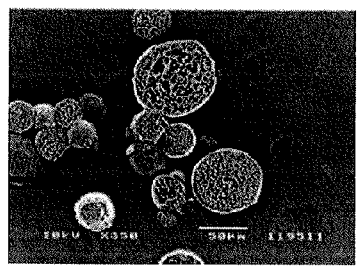 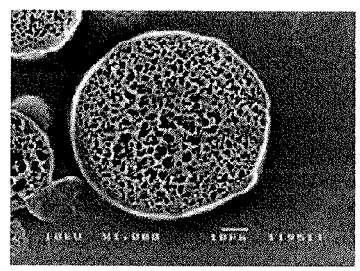 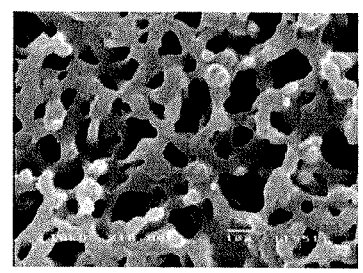
FIG. 14I  FIG. 14J  FIG. 14K
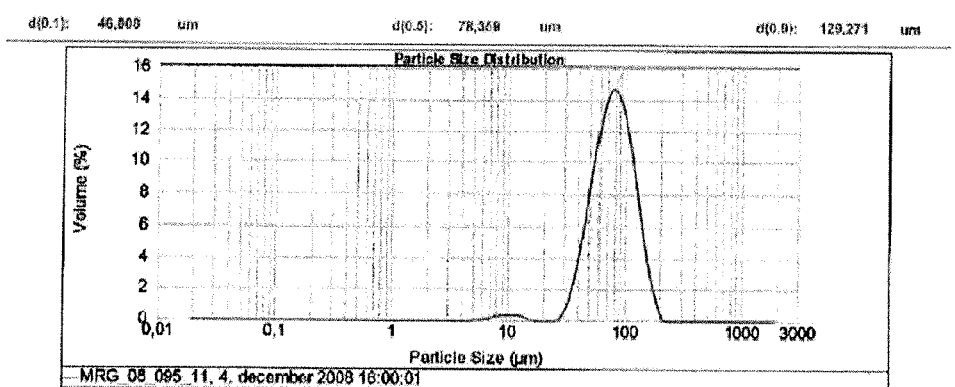
FIG. 14L

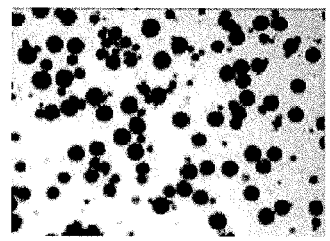
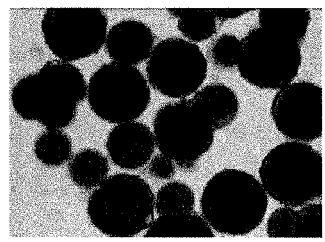
FIG. 15A   FIG. 15B
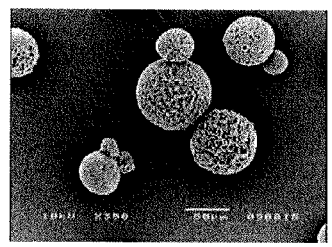
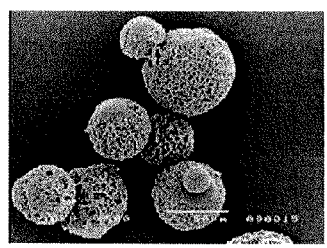
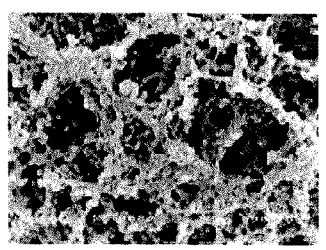
FIG. 15C   FIG. 15D   FIG. 15E
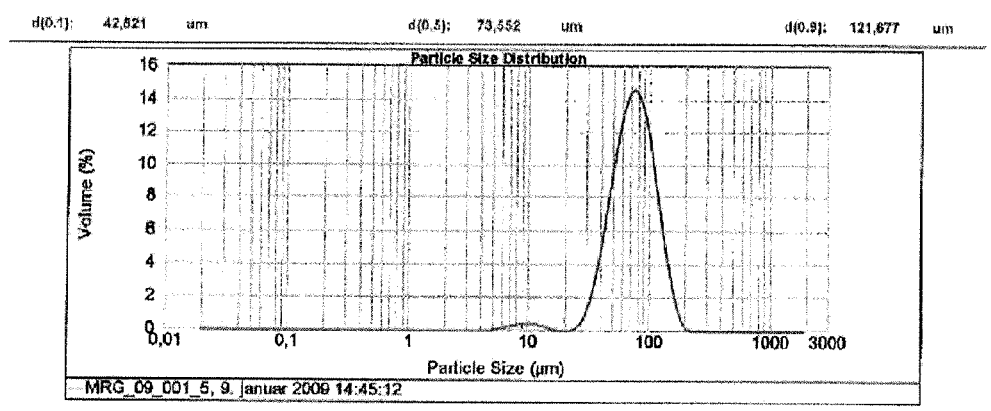
FIG. 15F

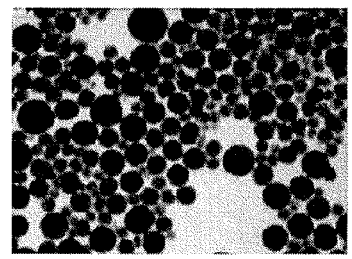 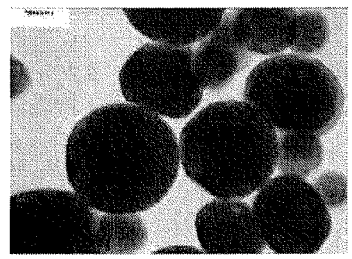
FIG. 17A    FIG. 17B
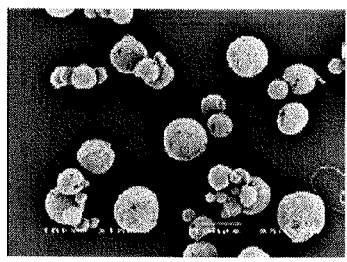 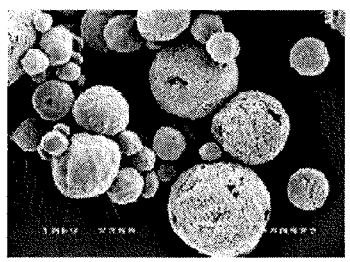 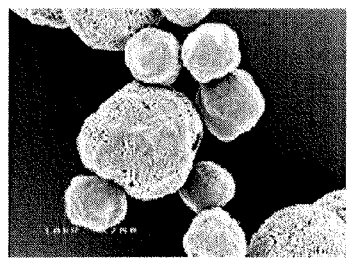
FIG. 17C    FIG. 17D    FIG. 17E

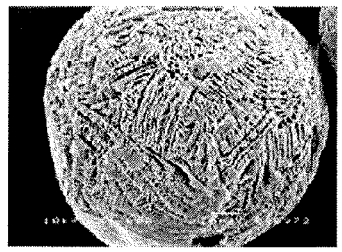  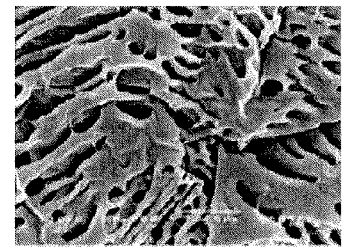
FIG. 17F  FIG. 17G  FIG. 17H
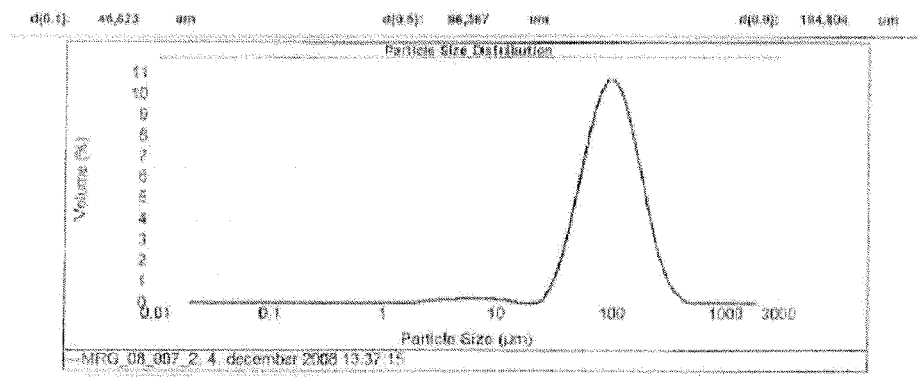
FIG. 17I

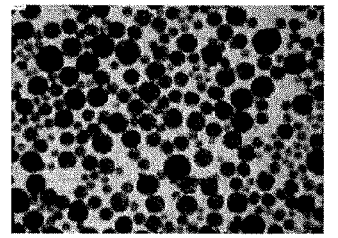
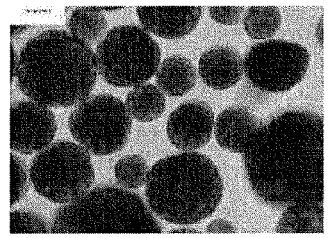
FIG. 18A    FIG. 18B
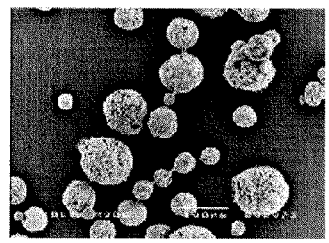
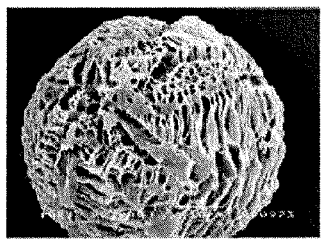
FIG. 18C    FIG. 18D    FIG. 18E
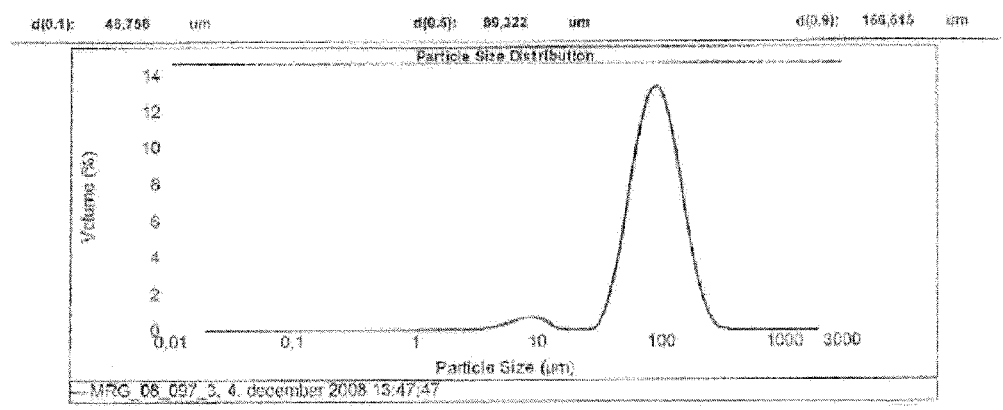
FIG. 18F

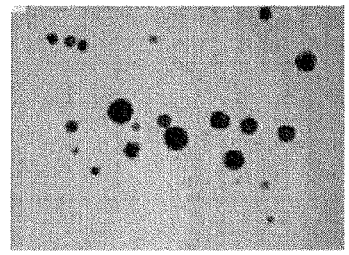 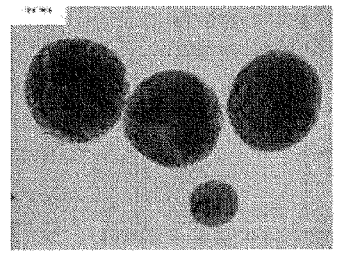
FIG. 19A  FIG. 19B
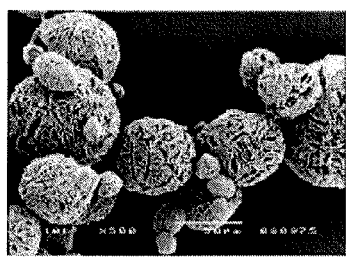 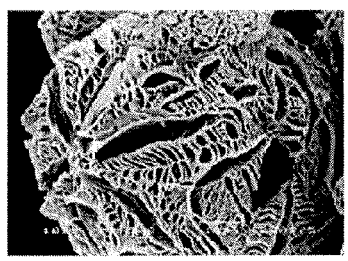 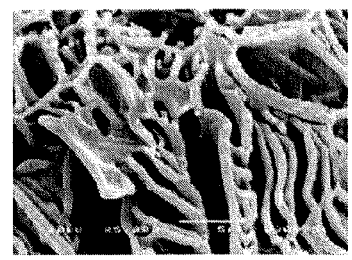
FIG. 19C  FIG. 19D  FIG. 19E
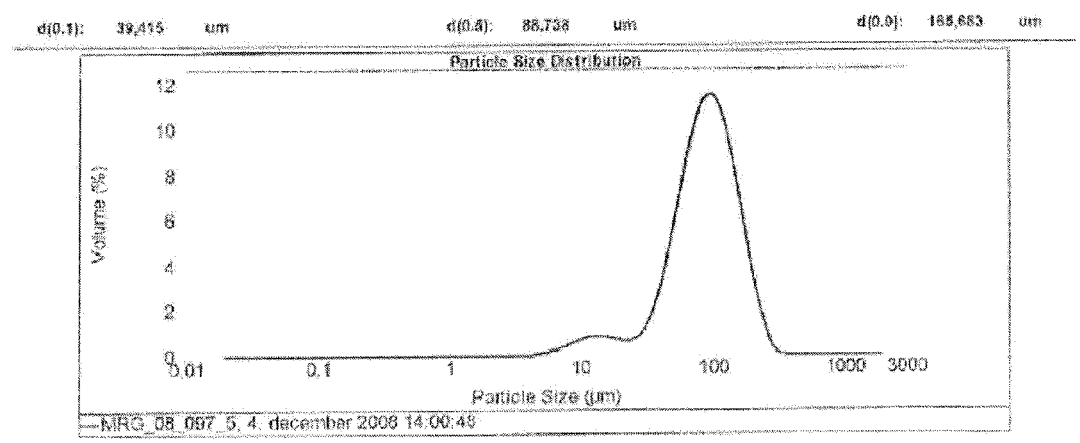
FIG. 19F

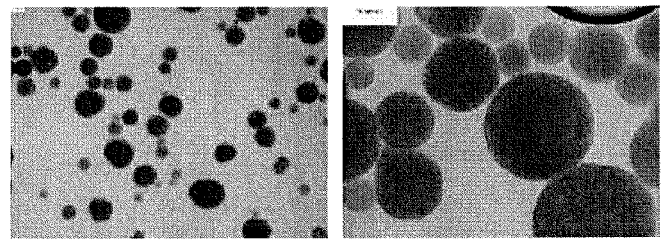
FIG. 20A    FIG. 20B
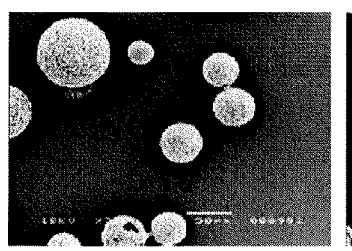  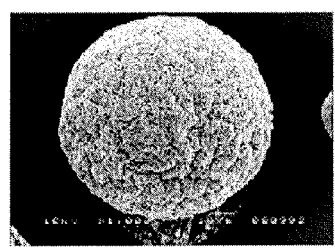  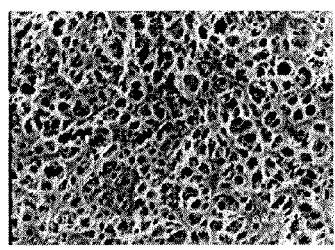
FIG. 20C    FIG. 20D    FIG. 20E
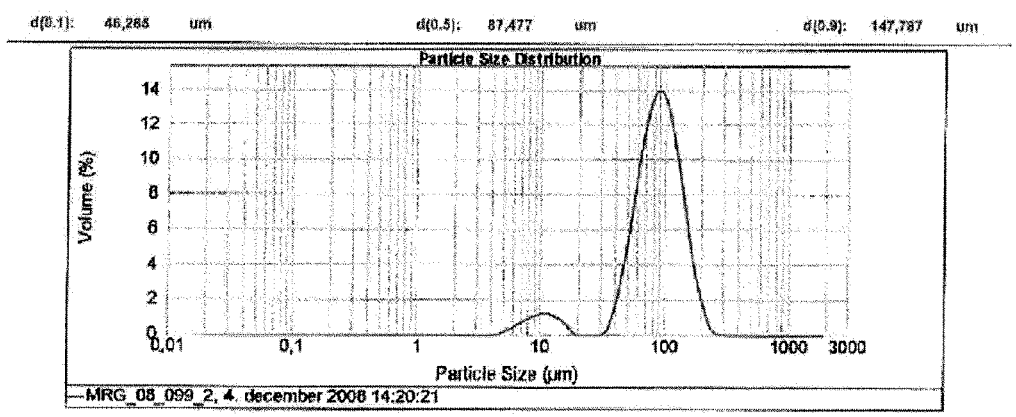
FIG. 20F

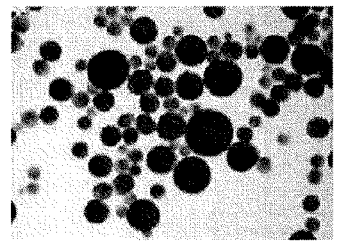
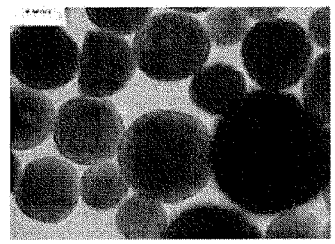
FIG. 21A  FIG. 21B
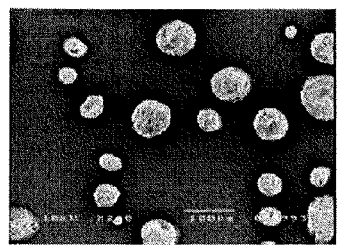
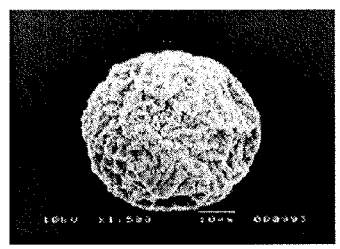
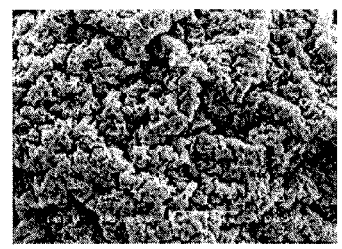
FIG. 21C  FIG. 21D  FIG. 21E
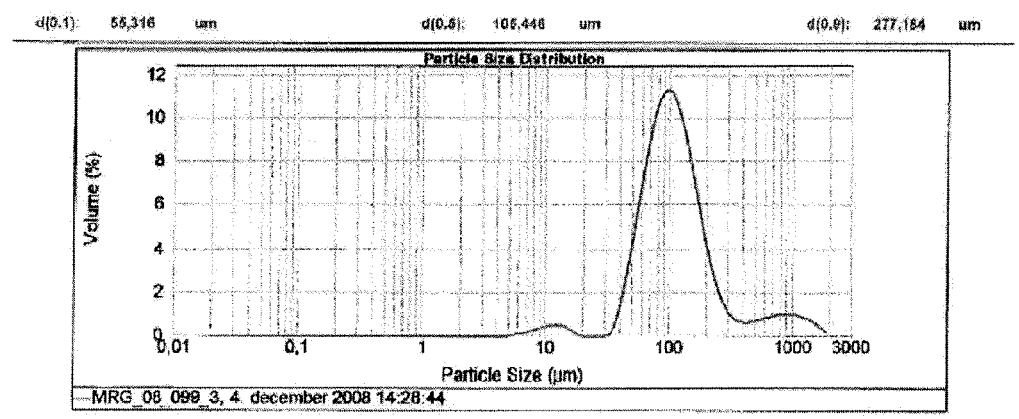
FIG. 21F

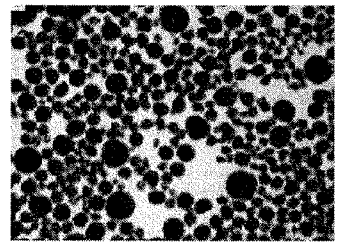
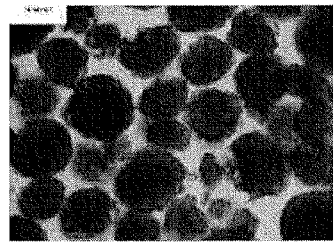
FIG. 22A  FIG. 22B
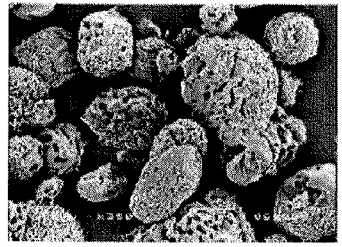
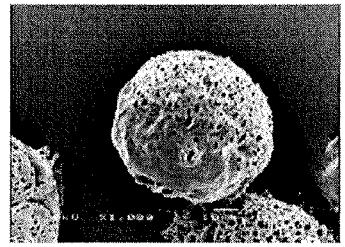
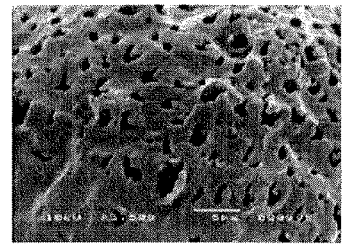
FIG. 22C  FIG. 22D  FIG. 22E
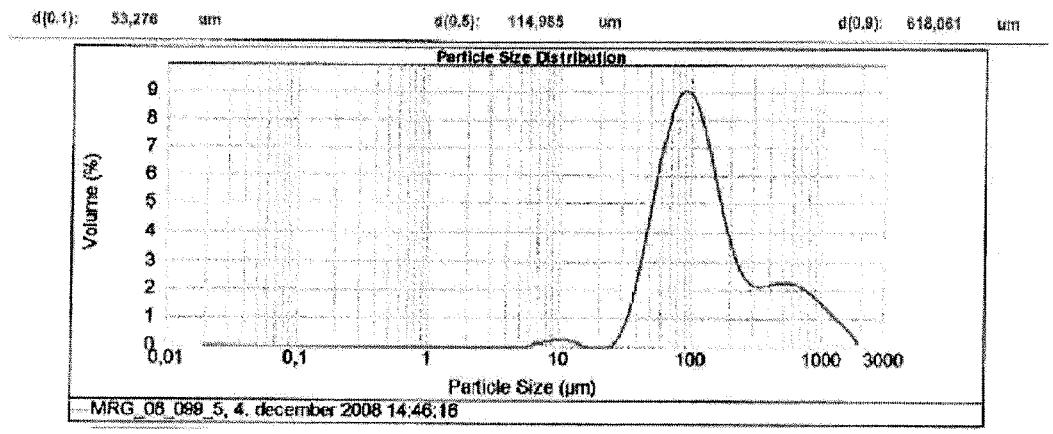
FIG. 22F

COMPOSITIONS AND METHODS FOR AUGMENTATION AND REGENERATION OF LIVING TISSUE IN A SUBJECT

This is a divisional of Ser. No. 12/735,976, filed, Aug. 27, 2010, which is a 371 of PCT/EP09/52461, filed Mar. 2, 2009, which has priority of Denmark no. PA 2008 00307 filed Feb. 28, 2008, the disclosures of which are incorporated herein by reference.

FIELD OF THE INVENTION

The present invention relates to compositions and methods suitable for the augmentation and regeneration of living tissue in a subject.

BACKGROUND OF THE INVENTION

Tissue engineering methods using cell transplantation are known, and for example, may involve for instance open joint surgery (e.g., open knee surgery) and, in case of joint surgery, extensive periods of relative disability for the patient to recuperate in order to ensure that optimal results are achieved. Such procedures are costly, and require extensive medical procedures such as rehabilitation and physical therapy.

Methods using scaffold technologies of various forms, where the scaffold (with, or without cells grown in the scaffold) is inserted into the defect, have suffered from difficulties in performing the cell implantation procedure solely guided by arthroscopy.

Arthroscopic Autologous Cell Implantation (called AACI or ACI using minor surgical interventions) is a surgical procedure for treating cartilage or bone defects, whereby a scaffold is inserted into the defect concomitantly with applying cell suspension or cell mixture with precursor fixatives, into said defect using a needle as for instance a "blunt" needle or a catheter. This implantation procedure is visualized and guided by an arthroscope.

WO 2004/110512 discloses an endoscopic method, useful for treating cartilage or bone defects in mammals, involving identifying the position of defect and applying chondrocytes, chondroblasts, osteocytes and osteoblasts cells into cartilage or bone defect. The cells are applied with a solidafiable support material, such as soluble thrombin and fibrinogen or collagen mixtures. It is envisaged that, for surgery in a convex or concave joint, that a porous membrane may be placed at the site of defect, but removed once the fibrin/cell mix are coagulated in place. The method disclosed in WO 2004/110512 allows tissues to be repaired arthroscopically, i.e. without the need of open joint surgery (e.g., open knee surgery).

Scaffolds are porous structures into which cells may be incorporated. They may be made up of biocompatible, biodegradable materials and are added to tissue to guide the organization, growth and differentiation of cells in the process of forming functional tissue. The materials used can be either of natural or synthetic origin.

WO 2007/028169 relates to a method for tissue engineering by cell implantation that involves the use of a scaffold in situ at the site of a defect, where the therapeutic cells are fixed in place into the scaffold only once the scaffold is inserted at the site of the tissue defect.

WO 2007/101443 provides preferred scaffold materials for use in the methods and kit of parts of the present invention.

Microparticles have been used as injectable scaffolds for tissue augmentation and support.

WO96/02209 reports on an injectable, biocompatible smooth surfaced carbon coated metallic particles (100-1000 microns in size) for use in combination with a lubricate fluid or gel for augmentation of the urinary sphincter muscle.

Xu and Reid et al. (Annals New York Academy of Sciences Vol. 944:144-159, 2001)) disclose the use of porous biocompatible and biodegradable (PLGA) microcarriers beads (spheres) of diameter 20-40 microns and 100-300 microns to attach hepatoma cells for the formation of three-dimensional cell-degradable microcarrier colonies in culture.

Kang et al. (J. Biomater. Sci. Polymer Edn, Vol 17, No 8, pp 925-939 (2006) discloses the manufacture and use of PLGA microspheres as injectable carriers for cartilage regeneration in rabbit knees. The beads were filtered into a range of 30-80 micron beads. The smaller beads were discarded as they were considered they may migrate to distant organs after implantation.

The present invention provides new and improved compositions for augmentation and regeneration of living tissue in a subject.

BRIEF DESCRIPTION OF FIGURES

FIG. 1A is an optical microscopy, FIG. 1B is a SEM.

FIG. 3A is an optical microscopy, FIG. 3B is a particle size distribution graph, and each of FIGS. 3C-3J is a SEM for experiment 3.

FIG. 4A is an optical microscopy, FIG. 4B is a SEM, and FIG. 4C is a particle size distribution graph for experiment 4.

FIG. 5A is an optical microscopy, FIG. 5B is a SEM, and FIG. 5C is a particle size distribution graph for experiment 5.

FIG. 6A is an optical microscopy, FIG. 6B is a SEM, and FIG. 6C is a particle size distribution graph for experiment 6.

FIGS. 11A-11C, 12A-12C, 13A and 13B, 14A and 14B, and 15A and 15B are each an optical microscopy, FIGS. 11D-11F, 12D and 12E, 13C-13E, 14C-14K, and 15C-15F are each a SEM, and FIGS. 11G, 12F, 13F, 14L, and 15F are each a particle size distribution graph for experiments 7-11, as described in Example 7.

FIGS. 16A-16C, 17A and 17B, 18A and 18B, 19A and 19B, 20A and 20B, 21A and 21B, and 22A and 22B are each an optical microscopy, FIGS. 16D-16F, 17C-17H, 18C-18E, 19C-19E, 20C-20E, 21C-21E, and 22C-22E, are each a SEM, and FIGS. 16G, 17I, 18F, 19F, 20F, 21F, and 22F are each a particle size distribution graph for experiments 12-18, described in Example 8.

SUMMARY OF THE INVENTION

Figure 1C:
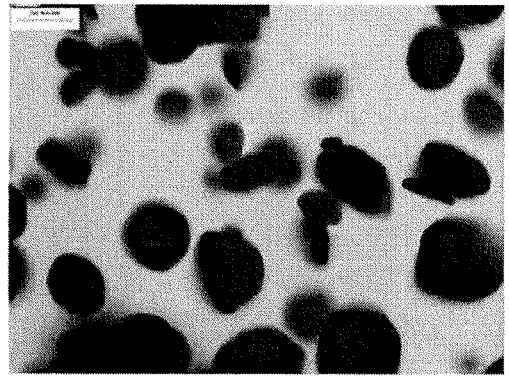
FIG. 1C is a particle size distribution graph for experiment 1.
Figure 1C:
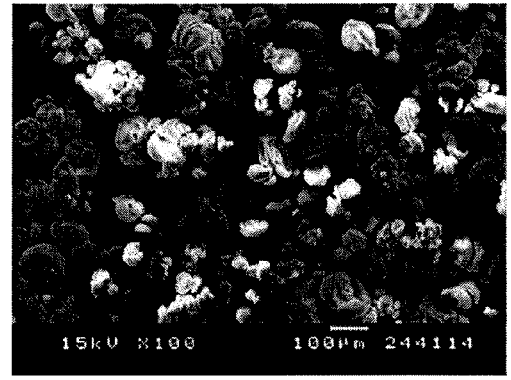
Figure 1C:
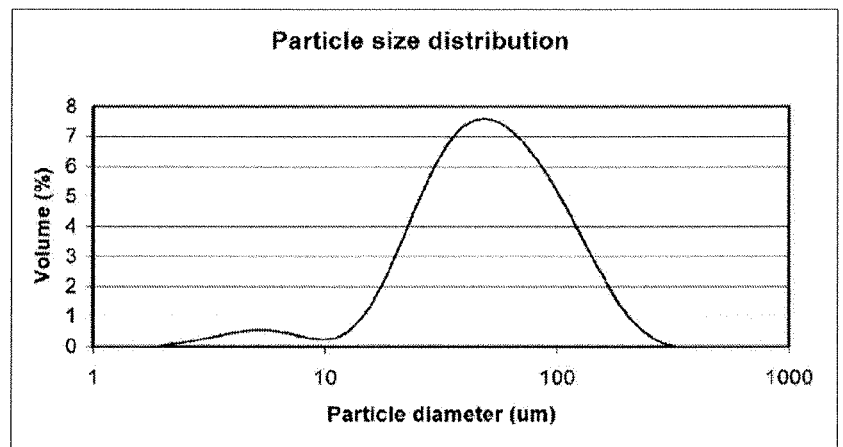

It has surprisingly been found by the inventors of the present invention that compositions comprising microparticles of a biodegradable polymer together with one or more mammalian cell populations provide particular suitable compositions for the augmentation and regeneration of living tissue in a subject.

The invention provides for a composition, for augmentation and regeneration of living tissue in a subject, comprising:
a. a population of microparticles of a biodegradable polymer,
b. one or more mammalian cell populations,
and optionally, a biocompatible adhesive.

The invention provides for a method for the preparation of a population of microparticles, preferably with a regular microparticle structure, such as microspheres, said method comprising:
a. Preparing a solution of the polymer in a solvent
b. Admixing the solution formed in step a) with a non-solvent
c. Atomise the solution formed in step b) into a non-solvent at below room temperature (preferably below 0° C.) to form the microparticles
d. Collect the particles formed, preferably by filtration,
e. Optionally dry particles, preferably by application of a vacuum or by freeze drying.

The invention provides for a method for the preparation of a population of microparticles, in particular microparticles with an irregular microparticle structure, said method comprising:
a. Preparing a solution of the polymer in a solvent
b. Admixing the solution formed in step a) with a non-solvent
c. Freeze dry the admixed solution formed in step b)
d. Collect the particles formed
e. Optionally size fractionate particles, preferably by sieving.

The invention provides for a method for the preparation of a population of microparticles (preferably with an irregular structure), said method comprising:
a. Preparing a solution of the polymer in a solvent
b. Atomise, for example by ultrasonic atomisation, the solution formed in step a) into a non-solvent at below room temperature (preferably below 0° C.) to form the microparticles
c. Collect the particles formed, preferably via filtration
d. Optionally dry particles, preferably by application of a vacuum or by freeze drying.

The invention provides of a method for the preparation of a population of microparticles, said method comprising:
a. Preparing a solution of the polymer in a solvent that can be freeze dried;
b. Atomise, for example by ultrasonic atomisation, the solution formed in step a) into a cold chamber, thereby freezing the drops to particles;
c. collect the particles formed,
d. dry particles by freeze drying.

The invention further provides for a microparticle population prepared by the method of the invention.

The invention provides for a microparticle of MPEG-PLGA.

The invention provides for a population of microparticles of MPEG-PLGA.

The invention provides for a composition comprising a population of microparticles according to the invention, which further comprises a biocompatible adhesive, and/or a further or other compound or compounds as referred to herein.

The invention provides for a method for the preparation of a composition wherein one or more population of a mammalian cell is attached to a population of microparticles of a biodegradable polymer, said method comprising the steps of:
a) contacting in vitro one or more population of a mammalian cell, as defined in any one of the proceeding claims with a population of microparticles of a biodegradable polymer, as referred to herein; and
b) culturing in vitro for a period of time said mammalian cells with said population of microparticles of a biodegradable polymer so that the mammalian cells attach to the microparticles.

The invention provides for a kit comprising
a. a compartment comprising a population of microparticles of a biodegradable polymer, and;
b. a compartment comprising one or more populations of mammalian cells, and optionally;
c. a compartment, which may be the same of different compartment to that referred to in a., comprising a biocompatible adhesive, and optionally;
d. a compartment with a conversion agent for said biocompatible adhesive,
Wherein the compartment referred to in a. is isolated from the compartment referred to in b.

The invention provides for a method for the regeneration or augmentation of a living tissue within a patient, said method comprising preparing the composition according to the invention and administering said composition into the living tissue to be regenerated or augmented, such as the living tissue referred to in any one of the preceding embodiments.

The invention provides for a microparticle, population of microparticles, or the composition according to the invention for use as a medicament.

The invention provides for a microparticle, population of microparticles, or a composition according to the invention for use in the treatment of a disease related to uro-gynaecological disorders such as urinary incontinence, pelvic organ prolapse, and anal incontinence.

The invention provides for a microparticle, population of microparticles, or a composition according to the invention for use in the treatment of a cartilage defect.

The invention provides for a microparticle, population of microparticles, or a composition according to the invention for use in the treatment of a bone defect, a bone disease or for bone regeneration.

The invention provides for the use of a microparticle, population of microparticles, or a composition according to the invention for the preparation of a medicament for use in the treatment of a disease related to uro-gynaecological disorders such as urinary incontinence, pelvic organ prolapse, and anal incontinence.

The invention provides for the use of a microparticle, population of microparticles, or a composition according to the invention for use in the preparation of a medicament for the treatment of a cartilage defect.

The invention provides for the use of a microparticle, population of microparticles, or a composition according to the invention for use in the preparation of a medicament for the treatment of a bone defect, bone disease or for bone regeneration.

DETAILED DESCRIPTION OF THE INVENTION

The invention provides microparticles of a biodegradable polymer for use in the composition, method and kit of the invention. The microparticles comprise or consist of biodegradable polymer(s), such as those described herein.

In a broad aspect the inventors of the present invention envision, that the microparticles along with cells according to the invention, or the composition according to the invention, may be used for reinforcing weakened tissue anywhere in the body.

One aspect of the invention relates to a sample of microparticles along with cells capable of growth. This sample is injected into or around areas responding to treatments with augmentive materials. In one embodiment, the sample is used for the treatment of urinary incontinence or vesicourethral reflux, urological disorders, where incontinence occurs when the resistance to urine flow has decreased to the point where the resistance can no longer resist the intraabdominal pressure. In another embodiment, the sample is used for treatment of anal sphincter incontinence, the microparticles may provide the bulking of the sphincter muscle providing in improvement of sphincter function. The sample may be injected into the tissue of the anal canal, wherein the selected site may be, for example, the internal or external anal sphincter tissue. The resulting bulking or augmentation of the tissue will restrict the size of the sphincter or anal passage and thus assist in overcoming fecal incontinence. Applicants also believe the present sample can be utilized in gastric reflux applications.

The composition may be injected into the tissue of the upper gastrointestinal tract, wherein the selected site may be, for example, the cardiac orifice of the stomach which opens into the esophagus. The resulting bulking or augmentation of the tissue will restrict the size of the passage and thus assist in overcoming gastric fluids refluxing into the esophagus. Common to all these examples is the fact that an immediate effect of the sample is obtained through the bulking effect. However, as the cells grow and the microparticles are degraded connective tissue is not formed but muscle, cartilage or other tissue is formed that will actively participate in re-generation of normal closure function.

In another embodiment, the invention relates to a sample of microparticles along with cells capable of regenerating bone tissue, such as osteoblasts and/or mesenchymal stem cells that have the ability to differentiate into mature osteoblasts in vivo, or can be induced to form mature osteoblasts in vitro. The cells could be either autologous, allogenic or xenogenic of origin. A composition containing such cells and the population of microparticles can be used for the repair of bone defects and for bone regeneration. The composition can therefore be applied to bone fractures in various bones of the human body, such as femur, tibia, hip, spinal, humerus, radius and ulna. Furthermore it could be used in bone augmentation procedures in patients with an atrophic maxilla (upper jaw bone) or mandible (lower jaw bone). The injectable characteristic of the composition is especially important for this clinical indication. It should be noted that for use for the treatment of bone defects or for bone regeneration, it is advantageous to use microparticles according to the invention, which contain hydroxyapatite and/or calcium phosphate, and/or a composition of the invention which further comprises hydroxyapatite and/or calcium phosphate, for example added as particles which may be independent (but within the composition) from the microparticles of the invention. Furthermore for use in bone defect repair or bone regeneration, the composition of the invention may also comprise (bone morphogenic proteins) BMPs, these are proteins have a very potent effect on osteoblasts or osteogenic differentiated mesenchymal stem cells.

The microparticles also provide a flexible scaffold in situ, providing a structure on which the cells, which may be from the population of mammalian cells, and/or cells from the tissue surrounding the defect, can grow and form new tissue—thereby regenerating living tissue.

The term microparticle as used herein refers to particle with a size of between 1 micron and 1000 microns. It will be appreciated that the size in this respect refers to the diameter or average diameter of the particles.

The microparticles in the population may, for example, take the form of flakes, filaments, powder, fibers, rods, spheres or any intermediate of the aforementioned forms.

In one embodiment the microparticles which form the population are irregular in shape.

In one embodiment, the microparticles in the population have a surface area/volume ratio greater than the surface are/volume ratio of a microsphere of the same average diameter with a perfect sphere shape, such as a surface are/volume ratio of at least 1.25×, such as 1.5× such as 2×, such as 4× of a microsphere of the same average diameter with a perfect sphere shape, such as measured by a Malvern Particle Analyzer as described in example 1.

Microparticles which are not essentially spherical or are irregular in shape may be characterized by showing an enhanced flow viscosity (as compared to an equivalent population of spherical or essentially spherical microspheres), and as such may be particularly useful in vivo, where it is desirable that the microparticles inserted are able to remain in the place of insertion and provide structural support and augmentation. It is also considered that such microspheres form matrices in vivo which are more stable in their interaction with the defect tissue surface, thereby providing a higher degree of mechanical robustness than equivalent spherical microparticles.

In one embodiment the microparticles are not spherical or essential spherical in shape.

In one embodiment, the microparticles do not have a smooth surface when analyzed at a resolution of 100× using a scanning electron micrograph.

In this regards it is, in some applications, considered advantageous to have microparticles which are irregular in shape, and/or have an irregular surface morphology, such as flakes. Such particles interact with each other to provide a flexible but rigid matrix in which the cells can grow in the body. Such microparticles are considered to be particularly useful for use in the repair of cartilage defects, but may also be useful for the repair of other tissues, such as smooth muscle or bone.

Other shapes of irregular microparticles include any form of flakes, filaments, fibers, rods, spheres or any intermediate of the aforementioned forms.

As shown in the examples, and FIGS. 1-6, it is possible to prepare irregular shaped solids by the use of sonication of the biodegradable polymer, and by varying the solvent used and the conditions, microparticles of varying average diameter and shape complexity can be formed.

However in one embodiment the microparticles may be spherical or essentially spherical or oval—typically such microparticles have a regular shape. In one embodiment, such microparticles may be considered to be used in the treatment of muscle defects, such as smooth muscle defects, such as sphincter incontinence.

It is recognized that whilst spheres are characterized by having a three-dimensional surface of which all points are equidistant from a fixed point (i.e. perfectly spherical), within the context of the present invention the term spherical may include shapes that resemble spheres in that they do not have any defined corners or edges, but may not be perfectly radially symmetrical, and may therefore includes solid shapes which have a egg or oval shape—such shapes are considered to be encompassed by the term essentially spherical.

In a preferred embodiment, in the context of the composition of the invention, and methods of treatments, the mammalian cells, or at least a proportion of the mammalian cells, are attached to, or even within, the microparticle scaffold. This provides the advantage that the cells and scaffold are intricately associated upon insertion into the patient.

Prior to use, the microparticles of a biodegradable polymer are typically sterilised, and the preparation of the composition of the invention is performed, with the exception of the addition of the population of mammalian cells, under sterile (aseptic) conditions. This allows the preparation of compositions which can be used directly in medical treatment.

The invention provides methods for the preparation of microparticles which comprise or consist of the scaffold, such as MPEG-PLGA.

Microparticles of MPEG-PLGA may be prepared as described in the examples. A preferred method involves the preparation of a solution of the polymer in a suitable solvent, typically an organic solvent. The polymer solution is atomised, to form a suspension of microparticles. The microparticles are optionally filtered and then dried, for example under a vacuum.

It should be noted that the methods for the preparation of microparticles herein are not necessarily limited to biodegradable polymers, but are applicable to other polymers or polymer systems.

In one embodiment, the microparticles comprise or consist of a polymer, selected from the group consisting of: a) Homo- or copolymers of: glycolide, L-lactide, DL-lactide, meso-lactide, e-caprolactone, 1,4-dioxane-2-one, d-valerolactone, β-butyrolactone, g-butyrolactone, e-decalactone, 1,4-dioxepane-2-one, 1,5-dioxepan-2-one, 1,5,8,12-tetraoxacyclotetradecane-7-14-dione, 1,5-dioxepane-2-one, 6,6-dimethyl-1,4-dioxane-2-one, and trimethylene carbonate; b) Block-copolymers of mono- or difunctional polyethylene glycol and polymers of a) mentioned above; c) Block copolymers of mono- or difunctional polyalkylene glycol and polymers of a) mentioned above; d) Blends of the above mentioned polymers; and e) polyanhydrides and polyorthoesters.

Microparticles of a polymer may also be formed by adding a non-solvent to the solution of the polymer (i.e. a polymer in which the polymer is not soluble (or essentially not-soluble))—until the polymer particles come out of solution (i.e. the non-solvent is added until the system reaches the non-solvent boundary). The preparation of particles in such systems nearing the non-solvent boundary results in particles.

With reference to the term 'essentially non-soluble' it will be noted that, in some instances, a very slight degree of solubility of the polymer may be measurable, but that the level of solubility is insufficient to prevent the formation of microparticles in the method of the invention.

As can be seen in FIGS. 1-6 by varying the organic solvent different forms of microparticles may be prepared, with varying average size ranges, and shapes which vary from essentially spherical to irregular shapes. In further detail, by adding a non-solvent to a solution of polymer, you will eventually get to a point where the solvent of the solution transitions to a non-solvent and the polymer begins to precipitate. The boundary between a good and a bad solvent for a polymer is called a theta-solvent. In the examples herein it can be seen that a solution of polymer in a solvent system close to or with some distance to the non-solvent boundary (acetone/ethanol) gives spherical particles. In contrast the solutions in good solvents give rise to particles of more irregular shape.

The suitable organic solvent may be, in one embodiment, selected from the group consisting of acetone and dimethylcarbonate.

Suitable organic solvent for the polyesters mentioned above, may be in some embodiments chloroform, dichloromethane, acetone, butanone, tetrahydrofurane, dioxane, dimethylcarbonate.

The solvent may in one embodiment, be selected from the group consisting of chloroform, dioxane, acetone, methylacetate etc.

The non-solvents may in one embodiment be selected from the group consisting of the lower alcohols, such as methanol, ethanol, 1-propanol, 2-propanol, 1-butanol, 2-butanol, isobutanol, and t-butanol, diethyl ether, diisopropyl ether, hexane, alkanes, cycloalkanes and water.

The concentration of polymer prepared in the solution may be between, for example, 1 and 20%, such as between 2 and 10% (w/v).

We therefore consider that solvent systems in proximity of the non-solvent boundary will give rise to spherical particles under similar conditions.

An alternative method for preparing micro-particles is by freeze drying: Freeze drying of the scaffold is considered an advantageous method for the preparation of irregular shaped microparticles, such as flakes. Whilst microparticles may be prepared by freeze drying followed by a mechanical disruption of the solid polymer prepared, we have, as is shown in the examples, provided a method whereby it is possible to freeze dry polymer solution to form a powdered preparation. In one embodiment the powder is in the form of flakes. For freeze drying to be practical, a solvent is needed that has an appreciable vapor pressure below its freezing point. Few solvents that fulfil this criteria—suitably solvents are selected on basis of their high melting temperature, such as 1,4-dioxane, dimethylcarbonate, benzene, DMSO, or 1,1,1,3,3,3-hexafluoro-2-propanol. In one embodiment, the solvents are selected by basis that they are good solvents for polyesters, examples are 1,4-dioxane, or dimethylcarbonate. As illustrated in the examples, freezedrying makes them hollow/porous all the way through the particle.

Once the microparticles have been prepared, they may, optionally be dried and, if required, sieved to obtain particles of the desired size or size range. In one embodiment, the microparticles are sieved by wet sieving before drying.

A particular advantage of the processes described is that they do not rely on water as a solvent. For a most biodegradable scaffolds, hydrolysis is part of the degradation process, a process catalysed by presence of water. By not using water, such premature degradation is avoid. In the alternative, useful volatile solvents has been identified. Through the use of such solvents, we can dry the particles at low temperatures, thereby avoiding their melting.

The term "mammalian cell population", which may also be referred to as "mammalian cells" or "cells" herein, refers to any population of cells that are obtained from or derived from cells obtained from a mammalian tissue. In one embodiment "mammalian cell population" refers to a population of cells derived from a single cell clone, thereby being genotypic and phenotypic identical.

In some embodiments of the invention, more than one type of cells is used, which is therefore referred to as one or more mammalian cell populations. Preferably the cells are adherent cells.

In some embodiments of the invention, more than one type of cells is used as according to following table:

| Cell types in co-culture (together with microparticles) | Suitable for use in the clinical application: |
|---|---|
| Osteoblasts - Chondrocytes | Osteoarthritis |
| Mesenchymal stem cells - periodontal ligament cells | Regeneration of periodontal tissue (Periodontitis) |
| Smooth muscle cells - urothelial cells | Bladder regeneration |
| Umbilical vein endothelial cells - fibroblasts | Angiogenesis improvement |
| Hepatocytes - hepatic stellate cells | Hepatic regeneration |
| Keratinocytes - fibroblasts | Skin regeneration |
| Mammary epithelial cells - preadipocytes | Breast reconstruction |
| Respiratory epithelial cells - chondrocytes | Tracheal regeneration |

In one aspect of the invention the treatment or use is as according to one or more of the treatments or uses referred to in the table above.

In one aspect of the invention the population(s) of mammalian cells comprises one or more of the cell types referred to in the above table.

Preferably the cells have been maintained or cultured in vitro, prior to use in the method according to the invention.

In one preferred embodiment, the term "mammalian cell population" refers to a population of chondrocytes, chondroblasts, osteocytes and osteoblasts, periodontal cells, and/or combinations thereof.

In one embodiment the term "mammalian cell population" refer to a population of myoblasts, or stem cells which are capable of differentiating into myoblasts.

In one embodiment the term "mammalian cell population" refer to a population of osteoblasts, or stem cells which are capable of differentiating into osteoblasts.

In one embodiment the term "mammalian cell population" refer to a population of chondrocytes, or stem cells which are capable of differentiating into chondrocytes.

In a preferred embodiment, the cells are obtained from or derived from the living individual mammal, i.e. are autologous. The cells may also be homologous, i.e. compatible with the tissue to which they are applied, or may be derived from multipotent or even pluripotent stem cells, for instance in the form of allogenic cells. In one embodiment the cells may be allogenic, from another similar individual, or xenogenic, i.e. derived from an organism other than the organism being treated. The allogenic cells could be differentiated cells, progenitor cells, or cells whether originated from multipotent (e.g., embryonic or combination of embryonic and adult specialist cell or cells, pluripotent stemcells (derived from umbilical cord blood, adult stemcells, etc.), engineered cells either by exchange, insertion or addition of genes from other cells or gene constructs, the use of transfer of the nucleus of differentiated cells into embryonic stemcells or multipotent stem cells, e.g., stem cells derived from umbilical blood cells.

Therefore in one embodiment, the method of the invention also encompasses the use of stem cells, and cells derived from stem cells, the cells may be, preferably obtained from the same species as the individual mammal being treated, such as human stem cells, or cells derived there from.

In one embodiment the stem cells are embryonic stem cells.

In specific embodiments, particularly for repair of cartilage, and/or bone, the cells are mesenchymal cells or chondrogenic cells.

In further specific embodiments the mammalian cells are obtained or derived from adipose tissue or skin.

In further specific embodiments the mammalian cells are obtained or derived from the same individual mammal that is to be treated according to methods of the invention. Such methods of obtaining and culturing cells from the individual mammal are disclosed in WO02/061052.

The mammalian cells are supplied preferably in the form of a cell suspension or tissue explant. Tissue explants may be directly taken from any suitable parts of the individual mammal.

Tissue explants may, in one embodiment be macerated prior to, or whilst in contact with the microparticles, and as such provide individual cells or groups of cells which are connected together.

In one embodiment the cells used in the composition of the invention, may be in a composition further comprising extracellular matrix proteins, such as, in the case of chondrocytes, cartilaginous matrix produced by these chondrocytes. It is to be understood that chondrocytes may be maintained in culture so as to secrete a cartilaginous matrix, which composition of both cells and cartilaginous matrix may be used according to invention as an alternative to cells without extracellular matrix proteins.

Alternatively, such composition of both cells and extracellular matrix proteins may be obtained from tissue explants.

The mammalian cells may be autologous, homologous (allogenic) or xenogenic in origin with respect to the living tissue to be treated according to the invention.

The mammalian cells may originate from multipotent or pluripotent stem cells.

In one embodiment, the mammalian cells may be selected from the group consisting of: fibroblasts, keratinocytes, chondrocytes, endothelial cells, osteoblasts, neural and periodontal cells. In one embodiment, the cells are of mesenchymal origin.

In one embodiment the mammalian cell population is chondrogenic cells, such as chondrocytes, which are particularly preferred for cartilage repair.

The terms "chondrogenic cells" or "chondrogenic cell", refers to any cell that are obtained from or derived from cells obtained from a mammalian tissue, which may have been maintained or cultured in vitro, preferably in a suitable culture medium, prior to use in the method according to the invention and which is or may be developed into a chondrocyte.

It is envisaged that stem cells, or other suitable precursor cells which are capable of becoming or producing chondrocytes once in situ at the site of the defect may also be used.

The chondrogenic cells may be prepared as described in WO02/061052, which is hereby incorporated by reference.

The chondrogenic cells are typically mammalian chondrogenic cells, which in some embodiments are obtained or derived from said individual mammal being treated according to the invention. Such methods of obtaining and culturing cells from the individual mammal are disclosed in WO02/061052.

The mammalian chondrogenic cells may be supplied in the form of a cell suspension or tissue explants. Tissue explants may be directly taken from other parts of the individual mammal, and may therefore be in the form of tissue grafts such as a knee meniscal graft.

The mammalian chondrogenic cells may be any chondrogenic cell suitable to produce biosynthetic cartilaginous matrix. Suitable chondrogenic cells may include a cultured chondrocyte, such as a cultured knee meniscal chondrocyte, chondrocyte-derived cell line such as CHON-001, CHON- 002 (ATCC® Number: CRL-2846™, CRL-2847™), or TC28 cells, chondrogenic cells as disclosed in US patent application 20050129673, 20060148077, 20030064511, 20020094754, U.S. Pat. No. 6,841,151, U.S. Pat. No. 6,558,664, U.S. Pat. No. 6,340,592.

Human articular chondrocytes are particularly preferred.

It is envisaged that stem cells, or any other suitable precursor cells which are capable of becoming or producing chondrocytes may also be used.

The cells used in the composition are present in a sufficient amount of cells to result in regeneration or repair of the target tissue or defect, such as of about $0.1 \times 10^4$ to about $10 \times 10^6$ cells/ml, or $0.1 \times 10^6$ cells/ml to about $10 \times 10^6$ cells/ml.

In one aspect, the cells used in the composition are present in a sufficient amount of cells to result in regeneration or repair of the target tissue or defect, such as of about $0.1 \times 10^4/0.1$ cm$^3$ to about $10 \times 10^6$ cells/0.1 cm$^3$, or $0.1 \times 10^6$ cells/0.1 cm$^3$ to about $10 \times 10^6$ cells/0.1 cm$^3$.

When the term "about" is used herein in conjunction with a specific value or range of values, the term is used to refer to both about the range of values, as well as the actual specific values mentioned.

Prior to use, the chondrogenic cells are typically placed in a suitable suspension with a culture media, which may optionally comprise growth hormones, growth-factors, adhesion-promoting agents, and/or physiologically acceptable ions, such as calcium and/or magnesium ions (see WO 2004/110512). It is highly preferably that the cell suspension does not comprise significant levels of blood serum, i.e. are essentially serum free, such as free of autologous or homologous blood serum, particularly if the serum contains components which may interfere with the formation of the fixative in situ at the defect site.

In a preferred embodiment, the mammalian cells are immuno-compatible with said living tissue. The use of non immuno-compatible mammalian cells may however be used, for example with immunosuppressive drugs.

The composition of the invention comprises a population of microparticles of a biodegradable polymer, one (or more mammalian cell populations) and optionally, a biocompatible adhesive.

Typically, the cells used are present in the composition in a sufficient amount of cells to result in regeneration or repair of the target tissue or defect, such as of about $0.1 \times 10^4$ to about $10 \times 10^6$ cells/ml, or $0.1 \times 10^6$ cells/ml to about $10 \times 10^6$ cells/ml.

In one aspect, the cells used in the composition are present in a sufficient amount of cells to result in regeneration or repair of the target tissue or defect, such as of about $0.1 \times 10^4/0.1$ cm$^3$ to about $10 \times 10^6$ cells/0.1 cm$^3$, or $0.1 \times 10^6$ cells/0.1 cm$^3$ to about $10 \times 10^6$ cells/0.1 cm$^3$.

The microparticles present in the composition of the invention may be present or added to the composition in an amount, for example, a level between 0.1 mg/ml to 300 mg/ml, such as between 0.1 mg/ml to 100 mg/ml.

The microparticles present in the composition of the invention may, for example, be present or added to the composition in an amount of at least 0.1 mg/ml, or at least 0.25 mg/ml, or at least 0.5 mg/ml, or at least 1 mg/ml, or at least 1.5 mg/ml, or at least 2 mg/ml, or at least 5 mg/ml, or at least 10 mg/ml, or at least 20 mg/ml, or at least 50 mg/ml, or at least 70 mg/ml, or at least 90 mg/ml, or at least 100 mg/ml.

The microparticles present in the composition of the invention may be present, for example, or added to the composition in an amount less than 300 mg/ml, or less than 250 mg/ml, or less than 200 mg/ml or less than 150 mg/ml or less than 100 mg/ml or less than 75 mg/ml, or less than 50 mg/ml, or less than 40 mg/ml, or less than 30 mg/ml, or less than 20 mg/ml, or less than 10 mg/ml, or less than 5 mg/ml.

It is recognised that the composition of the invention include living and possibly dividing (growing) cells, and as such the cell population density in the composition is preferably measured at the time at which the composition is initially prepared, but may, in one embodiment, be the cell population density immediately prior to use.

Whilst it should be recognised that the composition of the invention may comprise agents which enhance the association or adhesion of the cells to the microparticles, in one embodiment an adhesive agent or agents may be added to the composition—the purpose of which is to fix the composition at the site of insertion into the body or defect, as well as enhance the structural integrity of the inserted composition once inserted into the body. Whilst the it is considered that agents which enhance the association or adhesion of the cells to the microparticle in vitro, may, in one embodiment be the same (type of) agent as the adhesive, it is preferred that the adhesive or adhesive precursor is added to the composition immediately prior to use. The adhesive agent should be biocompatible, and as such typical surgical adhesives may be considered.

The adhesive is typically in the form of an adhesive precursor, which immediately prior to or during use, is converted to an adhesive in situ. The adhesive precursor may also be described as a fixative precursor. The conversion of the adhesive or fixative precursor may be initiated by any suitable means, although in one embodiment a cross-linking agent may be used.

Suitably the cells are applied and/or grown in the presence of a biologically acceptable fixative precursor, such as fibrinogen, which may be recombinantly prepared or isolated from a mammalian host cell.

In one embodiment, the concentration of fibrinogen used is 1-100 mg/ml.

In one embodiment the adhesive precursor is prepared with, or associated with, the microparticle—for example the fixative precursor may be combined to the biodegradable polymer during preparation of the microparticle so that the microparticle comprises both the biodegradable scaffold and the fixative precursor.

In one embodiment, the cells are applied in vivo in the presence of a conversion agent suitable of converting the fixative precursor into a fixative material.

In another embodiment a UV curable hydrogel based on hyaluronic acid may be used in same way as for fibrinogen. Photofix HA from Zimmer Orthobiologics is an example of such material.

It should be understood that other biologically acceptable fixatives (adhesives) may be used—what is important is that the fixative is added or activated immediately prior to or during the surgical procedure so as not to impede the administration of the composition of the invention, which typically is performed via injection, but allows the rapid formation of a fixed composition containing the population of cells and the microparticles at the site of injection. The use of microparticles allows for the formation of a scaffold in vivo which can allow sufficient movement at the site of repair, without hindering the ability of the composition to augment the tissue at the site of defect, whilst allowing for the regeneration of the tissue over time, by the gradual biodegradation of the scaffold component (microparticles), typically within the time frame of biological repair by the inserted population of mammalian cells, which may furthermore be assisted by in growth of cells from the surrounding tissue.

The use of a fixative allows the cells to be secured at the site of insertion, but furthermore fixes the microparticles at the site of insertion—this greatly reduces the risk associated with microparticles and/or the cells (or combination of both) moving to sites and organs distant to the site of treatment. The movement of the cells to distant and unpredictable organs can lead to inappropriate tissue growth elsewhere in the body, particularly if the cells used are isolated from cell suspension, where there is a risk of cellular differentiation including the formation of pre-cancerous or even cancerous cells. By fixing the cells at the site of injection, the repair of the defect and the fate of the injected cells can be easily monitored.

In one embodiment, the conversion agent is a cross-linking agent, such as thrombin, a thrombin analogue, recombinant thrombin or a recombinant thrombin analogue.

In one embodiment, the concentration of thrombin used is between 0.1 NIH unit and 150 NIH units, and/or a suitable level of thrombin for polymerizing 1-100 mg/ml fibrinogen.

It will be recognised that in the preparation of the adhesive in situ, when the adhesive is based on a two component system, what matters is that the components are combined in such as way that the adhesive forms (fixes) in vivo. A such in one embodiment, the cross-linking agent may form part of the composition according to the invention, to which the adhesive precursor may be added immediately prior to use.

The composition of the invention may comprise compounds or agents which enhance cell adhesion (or the interaction between the microparticles and the cells), such as an extracellular matrix component of any suitable tissue, such as extracellular matrix components from bladder, intestine, skin.

Accordingly, the composition of the invention may comprise compounds or agents which enhance cell adhesion (or the interaction between the microparticles and the cells), such as an agent selected from the group consisting of: chondroitin sulfate, hyaluronan, heparin sulfate, heparan sulfate, dermatan sulfate, growth factors, fibrin, fibronectin, elastin, collagen, such as collagen type I and/or type II, gelatin, and aggrecan.

Dermatan sulphate (DA) and/or hyaluronic acid (HA), are particularly preferred, especially in relation to compositions comprising chondrogenic cells.

In one embodiment the compound or agent which enhance cell adhesion (or the interaction between the microparticles and the cells) is incorporated into the biodegradable polymer (or microparticle) such as at a proportion of between about 0.1 and about 15 wt %.

The composition of the invention may comprise other components, including biologically acceptable: lubricants, isotonic buffers, antibiotics, growth factors, or stimulation molecule or cellular factors that control cellular differentiation of stem cells into the desired cell type.

It is envisaged that for some applications, the composition of the invention may comprise at least one stimulation molecule, which induces a signal transduction in chondroblast/chondrocytes and which is selected from the group consisting of collagen proteins such as collagen types II, VI, IX, and XI, proteoglycans such as aggregans, decorin, fibromodulin and biglycan, and non-collageneous proteins such as cryoprecipitate, fibronectin, vitronectin, fibronogen, fibrillin, kistrin, echistatin, von Willebrand factor, tenascin and anchorin CII.

In one embodiment, the composition may further comprise one or more non-synthetic biopolymers, such as polysaccharides, polypeptides, lignin, polyphosphate or polyhydroxyalkanoates, gelatin, hyaluronan, collagen, such as collagen type I and/or type II, alginate, chitin, chitosan, keratin, silk, cellulose and derivatives thereof, and agarose.

In one embodiment, the composition may further comprise a growth factors, such as such as Insulin-like growth factor 1 (IGF-1), MGF, or Transforming growth factors (TGFs), such as TGF-alpha or TGF-beta, or FGFs, such as FGF-1 or FGF-2.

In one embodiment, the composition may further comprise hydroxyapatite and/or calcium phosphate. These may be a component of the microparticles or a separate component of the composition, for example particles or microparticles comprising or consisting of hydroxyapatite and/or calcium phosphate.

In one embodiment the composition of the invention may further comprise bone morphogenic protein(s) (BMPs).

In previous disclosures made by K. Osther and others (e.g. WO9808469; WO02083878 WO03028545 and U.S. Pat. Nos. 5,759,190; 5,989,269; 6,120,514; 6,283,980; 6,379,367; 6,592,598; 6,592,599; 6,599,300; 6,599,301), cells are applied in a scaffold and cultured into the scaffold for some time prior to placing both the cells and the scaffold containing the cells in the target (e.g. cartilage defect). These methods do not make use of microparticles.

The present invention relates to a method for the preparation of a composition, wherein one or more populations of mammalian cells are attached to a population of microparticles of a biodegradable polymer, the method comprising the steps of:
a) contacting in vitro the one or more populations of mammalian cells, with a population of microparticles of a biodegradable polymer; and
b) culturing in vitro for a period of time the mammalian cells with this population of microparticles of a biodegradable polymer.

Preferably, during step b) the mammalian cells will attach to the microparticles to produce a microparticle/mammalian cell complex. It is to be understood that the mammalian cells will attach to grow on the surface or in the case of porous microparticles possibly within the microparticle.

The term "contacting in vitro", as used herein, refers to a step, wherein the mammalian cells are applied onto, together with or within the microparticles of a biodegradable polymer under in vitro conditions, i.e. under conditions of a controlled environment outside of a living mammal.

The term "culturing in vitro", as used herein, refers to a step, wherein the mammalian cells are maintained under in vitro conditions, i.e. under conditions of a controlled environment outside of a living mammal. Alternatively the skilled person may use the phrases that the "cells are grown", or "cells are proliferated" in vitro, which is also within the meaning of term "culturing". When cells are cultured in vitro tissue can be formed.

In this regards, the composition of the invention may be cultured for a period of time once the cells and the microparticles have been admixed. Typically, the culturing step may be for at least a few hours, e.g. between 1-24, or a few days, such as between 1 and 6 days or even a few weeks, such as between 1-6 weeks. Few in this context may be, for example, 2, 3, 4, 5, 6, 7, 8, 9, 10, 11, 12, 13, 14, 15, 16, 17, 18, 19, 20, 21, 22, 23, 24. Typically culturing will be performed with suitable culture conditions well known to the person skilled in the art. Some form of agitation is desirable to retain the identity of the individual microparticles.

Typically, the preparation of the composition is performed in a suitable media, such as a liquid media. We have found that once the microparticles have been added to the media, it is advantageous to apply a vacuum, which ensures that the media is distributed around and/or through (in the case of porous microparticles), which facilitates the distribution of the microparticles in the media. In such an embodiment, the cells may be contacted prior to, or preferably after the vacuum step.

The above method may further comprise the step of adding other components as described above, including agents which may enhance cellular adhesion. Such other components may form part of the microparticle or may be added to the media surrounding the microparticles and/or cells.

In particular aspects, the mammalian cells mixed with culture medium are placed on the surface of or at least in conjunction with the cell-free microparticles of a biodegradable polymer, usually in a culture dish or flask. The mammalian cells usually together with a component which facilitates the cell adhesion and/or in-growth are absorbed through the hydrophilic scaffold material.

The methods described may be applied using any mammalian cells for the preparation of a population of microparticles suitable for augmentation and/or regeneration of living tissue in a subject.

It is to be understood that once the mammalian cells have been applied to the microparticles of a biodegradable polymer, the cells can be allowed to migrate and/or grow through the polymer to fasten on the surface or within the structure of this polymer. In one embodiment the composition includes a component which facilitates cell adhesion and/or in-growth—which may in one embodiment, be incorporated into the microparticles.

The invention provides for a method for the regeneration or augmentation of a living tissue within a patient, said method comprising preparing the composition according to the invention and administering said composition into the living tissue to be regenerated and/or augmented.

The living tissue is typically part of a living individual mammal. Typically the living tissue to be treated has a defect which is treated by the above method.

Suitably, in a preferred embodiment, the administration is via injection.

It should be recognised that there may go a period of time between the initial preparation of the composition of the invention and its use in augmentation/regeneration of tissue in vivo. Indeed, it is considered that in many instances it may be beneficial to culture the population of mammalian cells with the microparticles—this allows for the adhesion of or growth of, the cells to, or even within the microparticles, but may also allow for the differentiation of stem cells into specific cell types, or the production of desirable extracellular matrices.

The "living individual mammal" is any living individual mammal suitable for implantation, and is preferably a human being, typically a patient. However the methods of the invention may also be applicable to other mammals, such as a dog, a horse or a goat.

The methods for implantation of the biosynthetic cartilaginous matrix according to the invention may be performed as, or during a method of surgery, such as a method of endoscopic, arthroscopic, or minimal invasive surgery, or conventional or open surgery.

In one embodiment, the implantation is performed during reconstruction surgery or cosmetic surgery.

The term "defect" as used herein refers to any detrimental or injured condition of a tissue, which is associated with existing, or future, loss of, or hindered function, disability, discomfort or pain. The defect is preferably associated with a loss of normal tissue, such as a pronounced loss of normal tissue, or loss of tissue function, e.g. in relation to sphincter muscle incontinence.

It is envisaged that the methods of the invention may be used prophylactically, i.e. to prevent the occurrence of defects, or for preventing the deterioration of an existing defect, or to prevent or reduce the severity of disease. The defect may, for example be a cavity in the tissue, a tear or wound in the tissue, loss of tissue density, development of aberrant cell types, or caused by the surgical removal of non-healthy or injured tissue etc.

In one embodiment, the defect could either an injured articular cartilage, an articular cartilage defect down to and/or involving the bone (osteoarthritis), a combination of cartilage and bone defect, a defect in bone which is surrounded by normal cartilage or bone, or a defect in a bone structure itself or be a bone structure that needs re-enforcement by addition of bone cells with scaffold as in the SCAS system. In one embodiment, the defect is in cartilage, such as articular cartilage defect.

In some embodiments one or more microfractures is purposely induced under clinical conditions at the site of implantation prior to application of the composition of the invention. It is expected that host cells from the mammal being treated will migrate from the microfractures to assist the implant in attachment to this implantation site. The use of microfracturing is considered to be particularly pertinent to treatment of cartilage or bone defects.

The term "tissue" as used herein refers to a solid living tissue which is part of a living mammalian individual, such as a human being. The tissue may be a hard tissue (e.g. bone, joints, and cartilage). The tissue may be selected from the group consisting of: cartilage, such as articular cartilage, bone, periodontal tissues, such as teeth-associated bone structures, teeth-associated ligaments and cementum, ligament, and tendon, muscle, such as smooth muscle or any other mesenchymal tissue.

In one specific embodiment, the tissue is a muscle. In such an embodiment, the population of cells is suitable myoblasts, or cells, such as stem cells which are capable of differentiating into myoblasts. The muscle may be a smooth muscle, such as a sphincter muscle.

In one embodiment, the invention provides for a method for the augmentation and/or repair of a sphincter muscle.

In one embodiment, the invention provides for a method for the treatment of incontinence such as anal or urinary incontinence.

In one embodiment, the tissue is bone—in such as case the defect may be a bone fracture, in various bones of the human body, such as femur, tibia, hip, spinal, humerus, radius and ulna, the tissue may be maxilla (upper jaw bone) or mandible (lower jaw bone).

The invention further relates to a kit comprising the following independent compartments
a. a compartment comprising a population of microparticles of a biodegradable polymer;
b. a compartment comprising one or more population of a mammalian cell, and optionally;
c. a compartment, which may be the same of different compartment to that referred to in a., comprising a biocompatible adhesive, and optionally;
d. a compartment with a conversion agent for said biocompatible adhesive,
wherein the compartment referred to in a. is isolated from the compartment referred to in b.

The kit may comprise a compartment, which may be the same or different as the compartments referred to in a., b. or c. wherein said compartment comprises the other compound or agent as referred to herein, such as growth factors, components which facilitates cell adhesion.

It will be recognised that the kit of parts comprises the components of the composition according to the invention, and it is used to prepare the composition according to the invention. In this regards, prior to use of the composition, the population(s) of mammalian cells are combined with the microparticles and optionally the adhesive (fixative precursor), and optionally one or more of the other components. The cells may be cultured in the presence of the microparticles for a period of time before use, optionally in the presence of an agent which enhances cell association with the microparticles. The adhesive, and optionally other components, may then be added immediately prior to use.

In a preferred embodiment, the kit of parts relates to a kit for cartilage repair and other defects where there is a cavity. Such kit preferably contains:

a) Spheres in a concentration of 300 mg/ml to form a paste. May contain and active ingredient;
b) Cells in a concentration of 1 mill pr cm$^2$ for a 2 mm deep defect;
c) tissue glue like a fibrin glue.
d) A device to use for placing the spheres in the defect. For example a syringe without a needle, but with a flexible outlet, ensuring that it is possible to get access to defects located at various positions within the joint, through an arthroscopic procedure.

A paste can be obtained by mixing particles with water in ranges of 20-60% w/w. Particles from Experiment 13 formed a paste when mixing 0.2 g of particles in 1 ml of water.

This kit, could also be formed without the cells of b).

In another preferred embodiment, the kit of parts relates to a kit for repair of a muscle, for example sphincter replacement. Such kit preferably contains:

a) Spheres in a concentration of 10-150 mg/ml to form a liquid. The spheres may contain and an active ingredient;
b) Cells in conc. of 1 mill cells per 50-100 mg;
c) A device for placing the cells in the muscle. For example a syringe with a needle.

Injectable suspension of particles can be obtained when mixing particles with water in ranges of 1 to 40% w/w. Particles from Experiment 3 formed a suspension that could be injected through a 23 G needle when mixing 0.4 g of particles in 1 ml of water.

This kit, could also be formed without the cells of b).

A preferred fixative (adhesive) material is fibrin.

In a preferred embodiment, the fixative material is in the form of a hydrogel, i.e. a gelating material capable of binding water, for example fibrin formed by the combination of the fixative precursor fibrinogen and the conversion agent thrombin.

The term "fixative precursor" as used herein refers to a compound or material that may be converted into a fixative material, usually by the action of another compound termed herein the "conversion agent".

In one embodiment, the conversion agent may be a cross-linking agent and/or a polymerization agent and/or gelating agent.

In a preferred embodiment the conversion of the fixative precursor to the fixative occurs via the application of a conversion agent. The addition of the conversion agent to the fixative precursor, preferably occurs immediately prior to, simultaneous to, or immediately after the application of the composition to the site of the defect—i.e. the effect of the conversion agent in converting the fixative precursor to a fixative, such as a gel/hydrogel or solid, occurs only once the cells are in place, at the site of the defect.

In one embodiment, the conversion agent is an enzyme suitable of converting a substrate into a gel, such as a fibrin gel.

In one embodiment the conversion agent is UV-light such as with Photofix HA.

In one embodiment, the biodegradable polymer is prepared in such a manner that it, prior to use, is "impregnated" with a i) fixative precursor or ii) the conversion agent, which is capable of retaining its activity (e.g., the thrombin analogues developed by HumaGene Inc., Chicago, Ill.). The subsequent addition of the i) conversion agent or ii) fixative precursor, immediately prior to, during or subsequent to application of the composition of the invention to the site of defect, effectively creates the adhesive in situ.

The fixative precursor used in some embodiments of the invention may be any form of biocompatible glue or adhesive, including gelation agents, which are capable of being absorbed by the porous scaffold and, when converted into the fixative capable of anchoring both the cartilaginous matrix to the scaffold and the cells to the scaffold.

WO 2004/110512, which is hereby incorporated by reference, provides several fixative precursors and specific examples of suitable combinations of fixative precursors and conversion agents. Suitably, the ratio of fixative precursor to conversion agent may be used to control both the rate at which the fixation occurs, and the level of support provided by the fixative.

Suitable fixative precursors may be a polysaccharide such as agarose or alginase or protein such as a protein selected form the group consisting of: fibrinogen, gelatin, collagen, collagen peptides (type I, type II and type III).

It is preferable that the fixative precursor is biocompatible, and may for example be human proteins which have either been obtained from humans, or alternatively recombinantly expressed. Human fibrinogen is a preferred fixative precursor, polymerizing for instance when exposed to for instance thrombin. Suitably, the fixative may be a biocompatible medical adhesive.

In one embodiment, such as when the fixative precursor is fibrinogen, the conversion agent is thrombin or a thrombin analogue. Other coagulation factors such as Factor XIII may be added to facilitate the conversion. In a specific embodiment, ions, or salts such as sodium, calcium or magnesium, etc. that may facilitate the thrombin cleavage effect on fibrinogen rendering a polymerization may be added. Thrombin of any origin may be used, although it is preferable that a biologically compatible form is used—e.g. human recombinant thrombin may be used in the treatment of human tissue defects. Alternatively other sources of thrombin may be used, such as bovine thrombin.

Fixation may take the form of forming a gel (i.e. gelation) such as a hydrogel which locks the cells into the scaffold, whilst allowing a suitable medium for cell migration and growth, thereby facilitating the growth of new cartilage tissue through the scaffold.

In one embodiment, the biologically acceptable fixative precursor is a biologically obtained or derived component, such as fibrinogen.

The fibrinogen may be in the form of recombinant fibrinogen (e.g., recombinant human fibrinogen from HumaGene Inc., Chicago, Ill., USA). Thus, the recombinant fibrinogen may be isolated from a recombinant mammalian host cell, such as a host cell obtained or derived from the same species as the individual mammal, or a transgenic host.

Alternatively, the fibrinogen is derived and purified from blood plasma, such as human blood plasma.

Suitable concentrations of fibrinogen used include 1-100 mg/ml.

In one embodiment, particularly when the fixative precursor is fibrinogen, the conversion agent may be selected from the group consisting of: thrombin, a thrombin analogue, recombinant thrombin or a recombinant thrombin analogue.

Suitable concentrations of thrombin used are between 0.1 NIH unit and 150 NIH units, and/or a suitable level of thrombin for polymerizing 1-100 mg/ml fibrinogen.

Standard NIH units refers to the routinely used National Institute of Health standard unit for measurement of Thrombin, which according to Gaffney P J, Edgell (Thromb Haemost. 1995 September; 74(3):900-3, is equivalent to between 1.1 to 1.3 IU, preferably 1.15 IU, of thrombin.

The term "Biocompatible" refers to a composition or compound, which, when inserted into the body of a mammal, such as the body of patient, particularly when inserted at the site of the defect does not lead to significant toxicity or a detrimental immune response from the individual.

When choosing the tissue glue, it is preferred to adjust curing such that spheres, cells and glue is mixed and applied (e.g. to the defect) before the glue is completely cured.

In one embodiment, the biodegradable polymer may be selected from the group consisting of: a) Homo- or copolymers of: glycolide, L-lactide, DL-lactide, meso-lactide, e-caprolactone, 1,4-dioxane-2-one, d-valerolactone, β-butyrolactone, g-butyrolactone, e-decalactone, 1,4-dioxepane-2-one, 1,5-dioxepan-2-one, 1,5,8,12-tetraoxacyclotetradecane-7-14-dione, 1,5-dioxepane-2-one, 6,6-dimethyl-1,4-dioxane-2-one, and trimethylene carbonate; b) Block-copolymers of mono- or difunctional polyethylene glycol and polymers of a) mentioned above; c) Block copolymers of mono- or difunctional polyalkylene glycol and polymers of a) mentioned above; d) Blends of the above mentioned polymers; and e) polyanhydrides and polyorthoesters.

In one embodiment, the biodegradable polymer may be selected from the group consisting of: collagen, alginate, polylactic acid (PLA), polyglycolic acid (PGA), MPEG-PLGA or PLGA.

In some embodiments the biodegradable polymer is hydrophilic.

It other embodiments the biodegradable polymer, or microparticles which comprise said biodegradable polymer, is porous to water and/or an isotonic buffer.

In one embodiment, the biodegradable polymer (essentially) consists or comprises, such as comprise a majority of, a polymer, or polymers, of molecular weight, such as average molecule weight, greater than about 1 kDa, such as between about 1 kDa and about 1 million kDa, such as between 25 kDa and 75 kDa.

In preferred embodiments the biodegradable polymer is synthetic.

The pores of the biodegradable polymer or microparticle may be partly occupied by a component which facilitates the cell adhesion and/or in-growth for regeneration of tissue, such as a component selected from the group consisting of: Chondroitin sulfate, hyaluronan, heparin sulfate, heparan sulfate, dermatan sulfate, growth factors, fibrin, fibronectin, elastin, collagen, gelatin, and aggrecan.

In one interesting embodiment, the amount of compounds which enhance cell migration and/or tissue regeneration, such as hyaluronic acid, is incorporated into the biodegradable polymer or microparticle, such as at a proportion of between about 0.1 and about 15 wt %, such as between 0.1 and 10 wt %, such as such as between 0.1 and 10 wt %. In one embodiment the level is below 15 wt %, such as below 10 wt % or below 5 wt %. In one embodiment the level is above 0.01 wt % such as above 0.1 wt %, or above 1 wt %.

As discussed above the biodegradable polymer or microparticle may consist or comprise any suitable biologically acceptable material, however in a preferred embodiment the scaffold comprises of a compound selected from the group consisting of: polylactide (PLA), polycaprolactone (PCL), polyglycolide (PGA), poly(D,L-lactide-co-glycolide) (PLGA), MPEG-PLGA (methoxypolyethyleneglycol)-poly (D,L-lactide-co-glycolide), polyhydroxyacids in general. In this respect the scaffold, excluding the pore space and any additional components, such as those which facilitates the cell adhesion and/or in-growth for regeneration of tissue, may comprise at least 50%, such as at least 60%, at least 70%, at least 80% or at least 90%, of one or more of the polymers provided herein, including mixtures of polymers.

PLGA and MPEG-PLGA are particularly preferred.

The biodegradable polymer or microparticles may be prepared by freeze drying a solution comprising the compound, such as those listed above, in solution.

In some embodiments, the biodegradable polymer or microparticle may have a porosity of less than 90%, such as less than 70%, such as less than 50%.

In some embodiments, the biodegradable polymer or microparticle is non-porous or essentially non-porous, e.g. has a porosity of less than 5%, less than 2% or even less than 1%.

In other embodiments, the biodegradable polymer or microparticle may have a porosity in the range of 20% to 99%, such as 50 to 95%, or 75% to 95%.

Porosity may be measured by any method known in the art, such as comparing the volume of pores compared to the volume of solid microparticle. This may be done by determining the density of the microparticle as compared to a substantially non-porous sample of the same composition as the microparticle. Alternatively, physical and chemical gas adsorption, (surface area by multipoint B.E.T. nitrogen adsorption for example), as well as mercury intrusion porosimetry or sedimentation techniques can be used.

One use of the porous microparticles provided though the hereby published examples is for implants to living beings, preferably humans. By providing porous particles, we obtain a balance between the structural integrity of the particles and implanting as little foreign material to the living being as possible. The structural integrity makes sure that the particles don't collapse during degradation, but can be replaced by tissue during cell growth. One disadvantage of implantation of foreign material, is that the degradation product from both MPEG-PLGA and PLGA is acid. Thus, less acid degradation products and less acidification of surrounding tissue is obtained through the porous structure and the little implanted material.

A further advantage of a porous particle is the rough surface obtained. Such rough surface makes it's easier for the cells to attach, grow and degrade the scaffold as tissue is formed.

In one embodiment the size of the microparticles is, on average, between 10 and 1000 microns, such as between 25 and 500 microns, such as between 20-400 microns, such as between 40 and 200 microns.

In one embodiment the size, or in one embodiment the average size, of the microparticles is less than 1000 microns, such as less than 700 microns, such as less than 500 microns, such as less than 400 microns, such as less than 300 microns, such as less than 200 microns or even less than 100 microns.

Selection of particles of a specified size range may be achieved, for example, by use of size cut off filters. Typically a range of sizes may be achieved initially, but particles of a preferred size range, for example between 20-100 microns, can be obtained by sieving through suitably sized filters.

In one embodiment the size, or in one embodiment the average size, of the particles is below 200 microns (in diameter), such as below 100 microns, such as below 75 microns, such as below 50 microns, such as below 40 microns, such as below 30 microns, such as below 20 microns, or is between 1 and 50 microns, such as between 1 and 40 microns, such as between 1 and 30 microns, such as between 1 and 20 microns, such as between 1 and 10 microns.

In one embodiment, the size (or average size) of the particles is at least 10 microns, such as at least 20 microns, such as at least 30 microns, such as at least 40 microns, such as at least 60 microns, such as at least 70 microns, such as at least 80 microns, such as at least 90 microns, such as at least 100 microns.

It is preferred that microparticles are small. That is, as described in the examples and figures, they have a distribution is size of 20-110 μm.

In one embodiment the biodegradable polymer or microparticle comprises a biological polymer, i.e. a biopolymer, such as protein, polysaccharide, lignin, polyphosphate or polyhydroxyalkanoates (e.g. as described in U.S. Pat. No. 6,495,152). Suitable biopolymers may be selected from the group consisting of: gelatin, collagen, alginate, chitin, chitosan, keratin, silk, cellulose and derivatives thereof, and agarose. Other suitable polymers or biopolymers include collagen IV or for example, other modified collagens (U.S. Pat. No. 6,676,969) that comprise natural cartilage material which has been subjected to defatting and other treatment, leaving the collagen II material together with glycosaminoglycans. Alternatively particles of purified collagen II may be mixed with glycosaminoglycans and any other required additives. Such additional additives may, for example, include chondronectin or anchorin II to assist attachment of the chrondocytes to the collagen II fibers and growth factors such as cartilage inducing factor (CIF), insulin-like growth factor (IGF) and transforming growth factor (TGFβ).

In some embodiments, the biodegradable polymer is hydrophilic, i.e. has the ability to absorb at least a small amount of water or aqueous solution (such as the cell suspension composition, e.g. the hydrogel solution), such as absorb at least 1%, such as at least such as at least 2%, such as at least 5%, such as at least 10%, such as at least 20%, such as at least 30%, such as at least 50% of the scaffold volume, of water (or equivalent aqueous solution) when placed in an aqueous solution, such as a physiological media, a buffer, or water. For some applications, it is beneficial that the polymer can absorb the above amounts of the cell suspension into its porous structure, thereby providing a relatively homogenous distribution of cells throughout the microparticle.

In some embodiments, the biodegradable polymer is at least partly hydrophilic, i.e. has a component of the polymer, which may be considered hydrophilic, such as an MPEG part of an MPEG-PLGA co-polymer.

The term hydrophilic is used interchangeably with the term 'polar'.

In the case when a non-polar polymer or microparticle is used, it is preferable that the polymer or microparticle is pretreated with an agent which facilitates the update of cells, such as a wetting agent. Wetting agents may also be used in conjunction with hydrophilic polymers to further improve cell penetration into the porous structure.

The microparticle may comprise or consist of a polyester. By incorporation of a hydrophilic block in the polymer or microparticle, the biocompatibility of the polymer or microparticle may be improved as it improves the wetting characteristics of the material and initial cell adhesion is impaired on non-polar materials.

In a highly interesting embodiment of the invention, the biodegradable polymer according to the invention consists or comprises of one or more of the polymers selected form the group comprising: poly(L-lactic acid) (PLLA), poly(D/L-lactic acid) (PDLLA), Poly(caprolactone) (PCL) and poly (lactic-co-glycolic acid) (PLGA), and derivatives thereof, particularly derivatives which comprise the respective polymer backbone, with the addition of substituent groups or compositions which enhance the hydrophilic nature of the polymer e.g. MPEG or PEG. Examples are provided herein, and include a highly preferred group of polymers, MPEG-PLGA.

In one embodiment, the scaffold consists or comprises a synthetic polymer.

WO 07/101,443 discloses suitable polymers for use as biodegradable polymers in the present invention as well as methods for their preparation.

Preferred biodegradable polymers for use in the method of the invention are composed of a polyalkylene glycol residue and one or two poly(lactic-co-glycolic acid) residue(s).

Hence, in one aspect of the for use in the method of the present invention the scaffold is prepared from, or comprises or consists of a polymer of the general formula:

wherein

A is a poly(lactide-co-glycolide) residue of a molecular weight of at least 4000 g/mol, the molar ratio of (i) lactide units and (ii) glycolide units in the poly(lactide-co-glycolide) residue being in the range of 80:20 to 10:90, in particular 70:30 to 10:90, more preferably in the region of 60:40 to 40:60 or about 50:50, including 50:50.

B is either a poly(lactide-co-glycolide) residue as defined for A or is selected from the group consisting of hydrogen, $C_{1-6}$-alkyl and hydroxy protecting groups, one of $R^1$ and $R^2$ within each —(CHR$^1$CHR$^2$O)— unit is selected from hydrogen and methyl, and the other of $R^1$ and $R^2$ within the same —(CHR$^1$CHR$^2$O)— unit is hydrogen, n represents the average number of —(CHR$^1$CHR$^2$O)— units within a polymer chain and is an integer in the range of 10-1000, in particular 16-250, the molar ratio of (iii) polyalkylene glycol units —(CHR1CHR2O)— to the combined amount of (i) lactide units and (ii) glycolide units in the poly(lactide-co-glycolide) residue(s) is at the most 20:80, and wherein the molecular weight of the copolymer is at least 10,000 g/mol, preferably at least 15,000 g/mol, or even at least 20,000 g/mol.

Hence, the polymers for use in the method of the invention can either be of the diblock-type or of the triblock-type.

It is understood that the polymer for use in the invention comprises either one or two residues A, i.e. poly(lactide-co-glycolide) residue(s). It is found that such residues should have a molecular weight of at least 4000 g/mol, more particularly at least 5000 g/mol, or even at least 8000 g/mol.

The poly(lactide-co-glycolide) of the polymer can be degraded under physiological conditions, e.g. in bodily fluids and in tissue. However, due to the molecular weight of these residues (and the other requirements set forth herein), it is believed that the degradation will be sufficiently slow so that materials and objects made from the polymer can fulfil their purpose before the polymer is fully degraded.

The expression "poly(lactide-co-glycolide)" encompasses a number of polymer variants, e.g. poly(random-lactide-coglycolide), poly(DL-lactide-co-glycolide), poly(mesolactide-co-glycolide), poly(L-lactide-co-glycolide), poly(D-lactide-co-glycolide), the sequence of lactide/glycolide in the PLGA can be either random, tapered or as blocks and the lactide can be either L-lactide, DL-lactide or D-lactide.

Preferably, the poly(lactide-co-glycolide) is a poly(random-lactide-co-glycolide) or poly(tapered-lactide-co-glycolide).

Another important feature is the fact that the molar ratio of (i) lactide units and (ii) glycolide units in the poly(lactide-co-glycolide) residue(s) should be in the range of 80:20 to 10:90, in particular 70:30 to 10:90, more preferably in the region of 60:40 to 40:60 or about 50:50, including 50:50.

It has generally been observed that the best results are obtained for polymers wherein the molar ratio of (i) lactide units and (ii) glycolide units in the poly(lactide-co-glycolide) residue(s) is 70:20 or less, however fairly good results were also observed when for polymer having a respective molar ratio of up to 80:20 as long as the molar ratio of (iii) polyalkylene glycol units —(CHR1CHR2O)— to the combined amount of (i) lactide units and (ii) glycolide units in the poly(lactide-co-glycolide) residue(s) was at the most 8:92.

As mentioned above, B is either a poly(lactide-co-glycolide) residue as defined for A or is selected from the group consisting of hydrogen, $C_{1-6}$-alkyl and hydroxy protecting groups.

In one embodiment, B is a poly(lactide-co-glycolide) residue as defined for A, i.e. the polymer is of the triblock-type.

In another embodiment, B is selected from the group consisting of hydrogen, $C_{1-6}$-alkyl and hydroxy protecting groups, i.e. the polymer is of the diblock-type.

Most typically (within this embodiment), B is $C_{1-6}$-alkyl, e.g. methyl, ethyl, 1-propyl, 2-propyl, 1-butyl, tert-butyl, 1-pentyl, etc., most preferably methyl. In the event where B is hydrogen, i.e. corresponding to a terminal OH group, the polymer is typically prepared using a hydroxy protecting group as B. "Hydroxy protecting groups" are groups that can be removed after the synthesis of the polymer by e.g. hydrogenolysis, hydrolysis or other suitable means without destroying the polymer, thus leaving a free hydroxyl group on the PEG-part, see, e.g. textbooks describing state-in-the-art procedures such as those described by Greene, T. W. and Wuts, P. G. M. (Protecting Groups in Organic Synthesis, third or later editions). Particularly useful examples hereof are benzyl, tetrahydropyranyl, methoxymethyl, and benzyloxycarbonyl. Such hydroxy protecting groups may be removed in order to obtain a polymer wherein B is hydrogen.

One of $R^1$ and $R^2$ within each —(CHR$^1$CHR$^2$O)— unit is selected from hydrogen and methyl, and the other of $R^1$ and $R^2$ within the same —(CHR$^1$CHR$^2$O)— unit is hydrogen. Hence, the —(CHR$^1$CHR$^2$O)$_n$— residue may either be a polyethylene glycol, a polypropylene glycol, or a poly(ethylene glycol-co-propylene glycol). Preferably, the —(CHR$^1$CHR$^2$O)$_n$— residue is a polyethylene glycol, i.e. both of $R^1$ and $R^2$ within each unit are hydrogen.

n represents the average number of —(CHR$^1$CHR$^2$O)— units within a polymer chain and is an integer in the range of 10-1000, in particular 16-250. It should be understood that n represents the average of —(CHR$^1$CHR$^2$O)— units within a pool of polymer molecules. This will be obvious for the person skilled in the art. The molecular weight of the polyalkylene glycol residue (—(CHR$^1$CHR$^2$O)$_n$—) is typically in the range of 750-10,000 g/mol, e.g. 750-5,000 g/mol.

The —(CHR$^1$CHR$^2$O)$_n$— residue is typically not degraded under physiological conditions, but may—on the other hand—be secreted in vivo, e.g. in from the human body.

The molar ratio of (iii) polyalkylene glycol units —(CHR$^1$CHR$^2$O)— to the combined amount of (i) lactide units and (ii) glycolide units in the poly(lactide-co-glycolide) residue(s) also plays a certain role and should be at the most 20:80. More typically, the ratio is at the most 18:82, such as at the most 16:84, preferably at the most 14:86, or at the most 12:88, in particular at the most 10:90, or even at the most 8:92. Often, the ratio is in the range of 0.5:99.5 to 18:82, such as in the range of 1:99 to 16:84, preferably in the range of 1:99 to 14:86, or in the range of 1:99 to 12:88, in particular in the range of 2:98 to 10:90, or even in the range of 2:98 to 8:92.

It is believed that the molecular weight of the copolymer is not particularly relevant as long as it is at least 10,000 g/mol. Preferably, however, the molecular weight is at least 15,000 g/mol. The "molecular weight" is to be construed as the number average molecular weight of the polymer, because the skilled person will appreciate that the molecular weight of polymer molecules within a pool of polymer molecules will be represented by values distributed around the average value, e.g. represented by a Gaussian distribution. More typically, the molecular weight is in the range of 10,000-1,000,000 g/mol, such as 15,000-250,000 g/mol. or 20,000-200,000 g/mol. Particularly interesting polymers are found to be those having a molecular weight of at least 20,000 g/mol, such as at least 30,000 g/mol.

The polymer structure may be illustrated as follows (where R is selected from hydrogen, C1-6-alkyl and hydroxy protecting groups; n is as defined above, and m, p and ran are selected so that the above-mentioned provisions for the poly(lactide-co-glycolide) residue(s) are fulfilled):

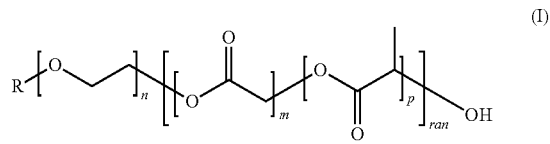

diblock-type polymer (I)

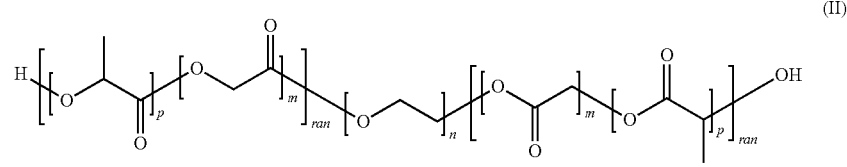

triblock-type polymer (II)

For each of the above-mentioned polymer structures (I) and (II) will be appreciated that the lactide and glycolide units represented by p and m may be randomly distributed depending on the starting materials and the reaction conditions.

Also, it is appreciated that the lactide units may be either D/L or L or D, typically D/L or L.

As mentioned above, the poly(lactide-co-glycolide) residue(s), i.e. the polyester residue(s), is/are degraded hydrolytically in physiological environments, and the polyalkylene glycol residue is secreted from, e.g., the mammalian body. The biodegradability can be assessed as outlined in the Experimentals section.

The polymers can in principle be prepared following principles known to the person skilled in the art.

In principle, polymer where B is not a residue A (diblock-type polymers) can be prepared as follows:

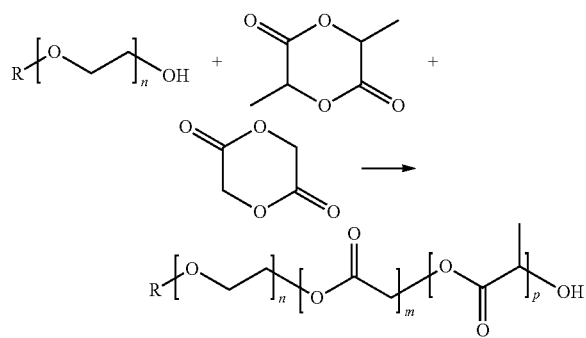

In principle, polymer where B is a residue A (triblock-type polymers) can be prepared as follows:

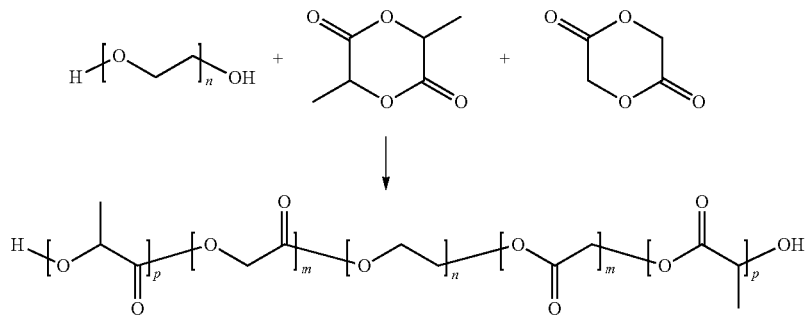

Unless special conditions are applied, the distribution of lactide units and glycolide units will be randomly distributed or tapered within each poly(lactide-co-glycolide) residue.

Preferably the ratio of glycolide units and lactide units present in the polymer used in scaffold is between an upper limit of about 80:20, and a lower limit of about 10:90, and a more preferable range of about 60:40 to 40:60.

Preferably the upper limit of PEG-content is at most about 20 molar %, such as at most about 15 molar %, such as between 1-15 molar %, preferably between 4-9 molar %, such as about 6 molar %.

In the present context, a biodegradable polymer means a polymer that disappears over a period of time after being introduced into a biological system, in vivo; the mechanism by which it disappears may vary, it may be hydrolysed, is broken down, is biodegraded/bioresorbable/bioabsorbable, is dissolved or in other ways vanish from the biological system. When used within a clinical context this is a huge clinical advantage as there is nothing to remove from the site of repair.

Thus, the newly formed tissue is not disturbed or stressed by presence of or even the removal of the temporary scaffold. It is typically preferred that the scaffold is broken down during 1 day to 10 weeks—depending on the application.

As shown in the examples, it is possible to measure the biodegradability of some polymers by utilising an in vitro model—and determine the in vitro degradation of a biodegradable polymer. In one embodiment, the polymer degrades in phosphate buffer, pH 7 at 60° C., so that no more than 5% of the polymer remains after, for example 10 days, or 20 days or 30 days.

For some polymers, such as PLGA based polymers, (bio) degradation occurs or involves to some extent a auto degradation process. This process can suitable be accelerated by the exogenous application of radiation. In one embodiment the degradation of the polymer may be accelerated, e.g. by the administration of a radiation source, such as beta-particles.

The biodegradability of polymers which are degraded by free radical decomposition, such as PLGA or MPEG-PLGA can be initiated by sterilisation or pre treatment, for example by beta-radiation.

It is possible to vary the degradation time of copolymers of DL-lactide and glycolide by varying the molar ratio of lactide and glycolide. Pure polyglycolide has a degradation time of 6-12 months, poly(D,L-lactide) 12-16 months, poly(D,L-lactide-co-glycolide 85:15 2-4 months. The shortest degradation is obtained with a 50:50 molar ratio, 1-2 months. It is also possible to vary the degradation time by varying the molecular weight, but this effect is small compared to the variations possible with the L:G-ratio (see report FIGS. 8 and 9). In theory is possible to get substantially faster degradation with very low molecular weight materials, but these have mechanical properties that preclude their use for most medical devices.

The synthesis of the microshperes and microparticles according to the invention is further illustrated in the Experimentals section.

The polymer or microparticles may, e.g. be a biodegradable, porous material with a specified porosity as described above.

The void space of the material of the polymer or microparticles may be unoccupied so as to allow or even facilitate cell adhesion and/or in-growth into the synthetic biodegradable polymer or microparticles. In one embodiment, the pores of the material are at least partly occupied by a component from the extracellular matrix. Examples of components from the extracellular matrix are chondroitin sulfate, hyaluronan, hyaluronic acid, heparin sulfate, heparan sulfate, dermatan sulfate, growth factors, fibrin, fibronectin, elastin, collagen, gelatin, and aggrecan.

As discussed elsewhere, the scaffold may also contain the conversion agent thrombin either alone or in combination with one of the above mentioned.

The components from the extracellular matrix could be added either as particles, which are heterogeneously dispersed, or as a surface coating. The concentration of the components from the extracellular matrix relative to the synthetic polymer is typically in the range of 0.5-15% (w/w), preferably below 10% (w/w). Moreover, the concentration of the components of the extracellular matrix is preferably at the most 0.3% (w/v), e.g. at the most 0.2 (w/v), relative to the volume of the material.

The porous materials may be prepared according to known techniques, e.g. as disclosed in Antonios G. Mikos, Amy J. Thorsen, Lisa A Cherwonka, Yuan Bao & Robert Langer. Preparation and characterization of poly(L-lactide) foams. Polymer 35, 1068-1077 (1994). One very useful technique for the preparation of the porous materials is, however, freeze-drying.

In one embodiment, the synthetic biodegradable polymer or microparticles is a scaffold of the polymer as prepared by the method disclosed in WO 07/101,443. The method is particularly suited to prepare scaffolds from PLGA and MPEG-PLGA polymers.

In some aspects of the present invention, the synthetic biodegradable polymer or microparticles is a scaffold prepared by the method disclosed in WO 07/101,443, which method comprises the steps of:
(a) dissolving a polymer as defined herein in a non-aqueous solvent so as to obtain a polymer solution;
(b) freezing the solution obtained in step (a) so as to obtain a frozen polymer solution; and
(c) freeze-drying the frozen polymer solution obtained in step (b) so as to obtain the biodegradable, porous material.
(d) optionally, and as necessary mechanically disrupting the material obtained in (c) and optionally size fractionating to the desired particle size.

The non-aqueous solvent used in the method as disclosed in WO 07/101,443 should with respect to melting point be selected so that it can be suitable frozen. Illustrative examples hereof are dioxane (mp. 12° C.) and dimethylcarbonate (mp. 4° C.).

In embodiments, wherein particles of components from the extracellular matrix is used in the methods according to the invention, these extracellular matrix components may be dispersed in the solution obtained in step (a) before the solution (dispersion) is frozen as defined in step (b).

The components from the extracellular matrix may, for instance, be dissolved in a suitable solvent and then added to the solution obtained in step (a). By mixing with the solvent of step (a), i.e. a solvent for the polymer defined herein, the components from the extracellular matrix will most likely precipitate so as to form a dispersion.

In one aspect, the biodegradable polymer or microparticles is immersed in a solution of glucosaminoglycan (e.g. hyaluronan) and subsequently freeze-dried.

EXAMPLES

In the following, PSD means Particle Size Distribution.

Example 1

Equipment
Sonics 20 kHz ultrasonic probe
Sonotek 25 kHz ultrasonic probe
NE-1000 syringe pump, New Era Pump Systems, Inc.
10, 25, 50 mL Hamilton syringes
Polymer solution led to ultrasonic probe by 1/16" PTFE-tubing
Polymer: MPEG-PLGA 2-30 kDa
Malvern Mastersizer 2000 with Hydro 2000s accessory for measuring suspensions.
Determination of particle size distribution: Particles were suspended in water with a small amount of sodium dodecyl sulfate and sonication and measured on the Malvern.
Optical miscroscopy: Olympus BX60, images were processed with Imagepro 5.1

Experiment 1:
A 4% (w/v) solution of polymer in acetone was atomized over a bath of stirred, cold (−50-(−30)° C.) isopropanol. The suspension was left to stir for 20 minutes and filtered cold with suction. The particles, were not sucked completely dry. They were dried in vacuum (0.04 mbar) for 24 h and stored in a closed vial until further characterization. FIG. 1A shows the optical microscopy, FIG. 1B shows the SEM, and FIG. 1C shows the particle size distribution for experiment 1.

Figure 2A:
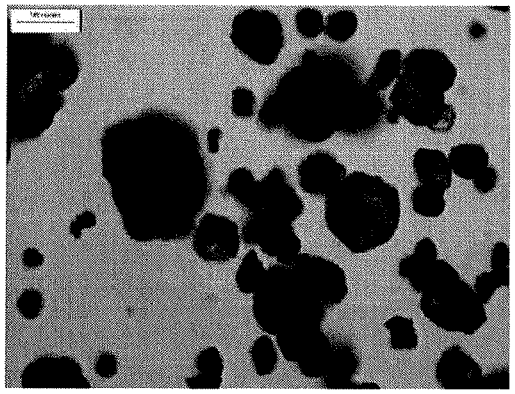
FIG. 2A is an optical microscopy.
Figure 2B:
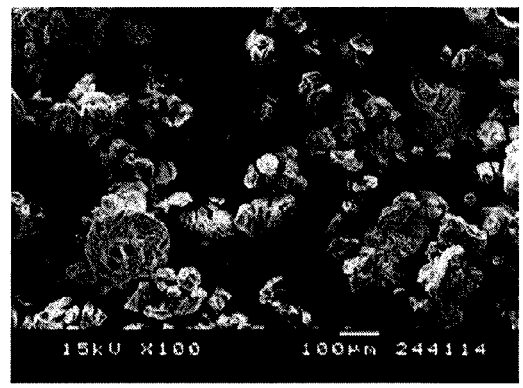
FIG. 2B is a SEM.
Figure 2C:
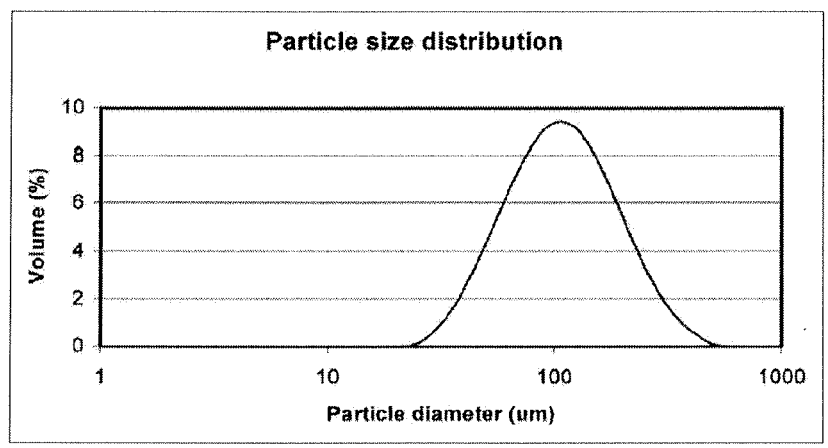
FIG. 2C is a particle size distribution graph for experiment 2.

Experiment 2:
A 10% (w/v) solution of polymer in acetone was atomized and collected as described in expt. 1. FIG. 2A shows the optical microscopy, FIG. 2B shows the SEM, and FIG. 2C shows the particle size distribution for experiment 2.

Experiment 3:
A 10% (w/v) solution of polymer in acetone was diluted with ethanol to 8.8% polymer in acetone/EtOH 86/14 and atomized (Ultrasonic atomizer, 25 kHz) and collected as described in experiment 1. FIG. 3A shows the optical microscopy, each of FIGS. 3C-3J shows a SEM, and FIG. 3B shows the particle size distribution for experiment 3.

Further characterization by SEM of particles obtained is shown in FIGS. 3C-3J. Visualization of the internal morphology of the particles was achieved by cryo slicing at −25° C. For this purpose, the particles were mounted in O.C.T.™ mounting medium from Tissue-Tek Sakura and visualized by SEM.

From these results is was apparent that the particles manufactured by this method are hollow with shells with a porosity in the nano range.

Experiment 4:
4% (w/v) in 1,4-dioxane, as in expt 1. FIG. 4A shows the optical microscopy, FIG. 4B shows the SEM, and FIG. 4C shows the particle size distribution for experiment 4.

Experiment 5:
4% (w/v) in dimethylcarbonate, as expt. 1. FIG. 5A shows the optical microscopy, FIG. 5B shows the SEM, and FIG. 5C shows the particle size distribution for experiment 5.

Experiment 6:
10% (w/v) in dimethylcarbonate, as expt. 1. FIG. 6A shows the optical microscopy, FIG. 6B shows the SEM, and FIG. 6C shows the particle size distribution for experiment 6.

Particles by Freeze Drying from a Solvent with an Added Non-Solvent:
Examples of suitable solvents: dioxane, dimethylcarbonate,
Examples of non-solvents: Water, methanol, ethanol, 1-propanol, 2-propanol, n-butanol, 2-butanol, isobutanol, t-butanol, pentane, isopentane, cyclopentane, hexane, cyclohexane, hexanes, heptane, heptanes.

Example 2

Figure 7A:
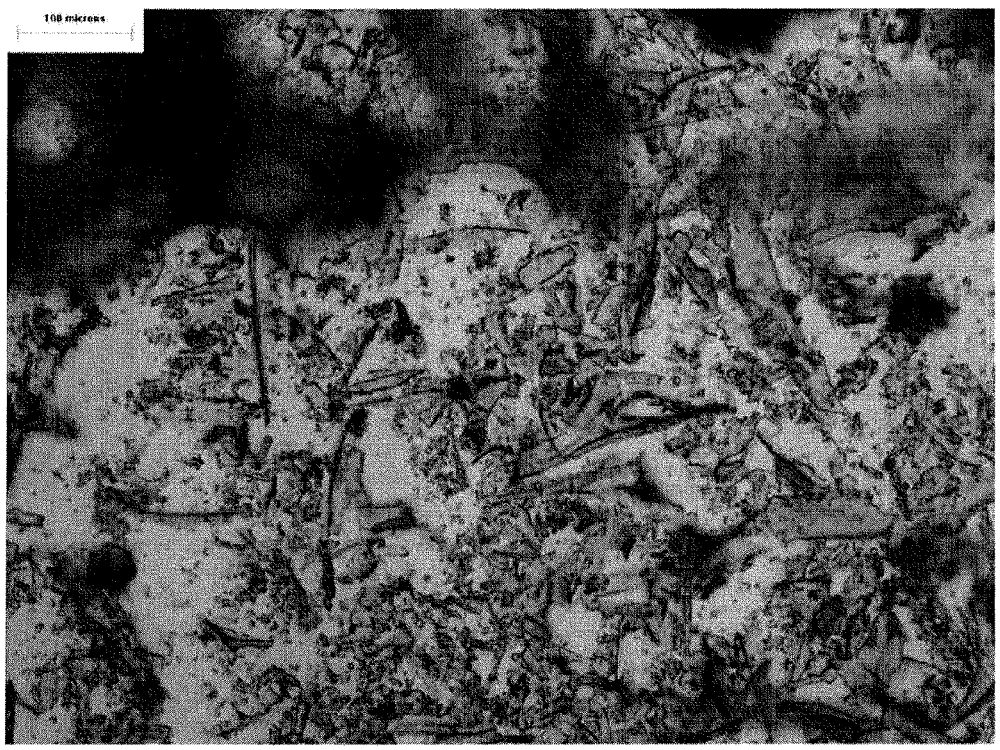
FIG. 7A is an optical microscopy of particles from Example 2.

2 g MPEG-PLGA 2-30 was dissolved in 100 ml 1,4-dioxane. To 50 mL of this solution was added 21.5 mL isopropanol (IPA). This solution is poured in an aluminium mould, and placed in the freeze dryer (shelf temperature −30° C.). When the solution is frozen, a mixture of 10 ml dioxane and 4.3 mL IPA is poured on top, and when this is frozen, vacuum is applied. The product was freeze dried with this program:
-30° C., 2 h
-20° C., 5 h
+20° C., 24 h The product prepared was a fluffy powder. A few larger flakes are removed by sieving through a 300 µm mesh. The powder is characterized by optical microscopy, and is seen to be composed of irregular pieces of polymer with a broad particle size distribution (FIG. 7a).

Example 3

Figure 7B:
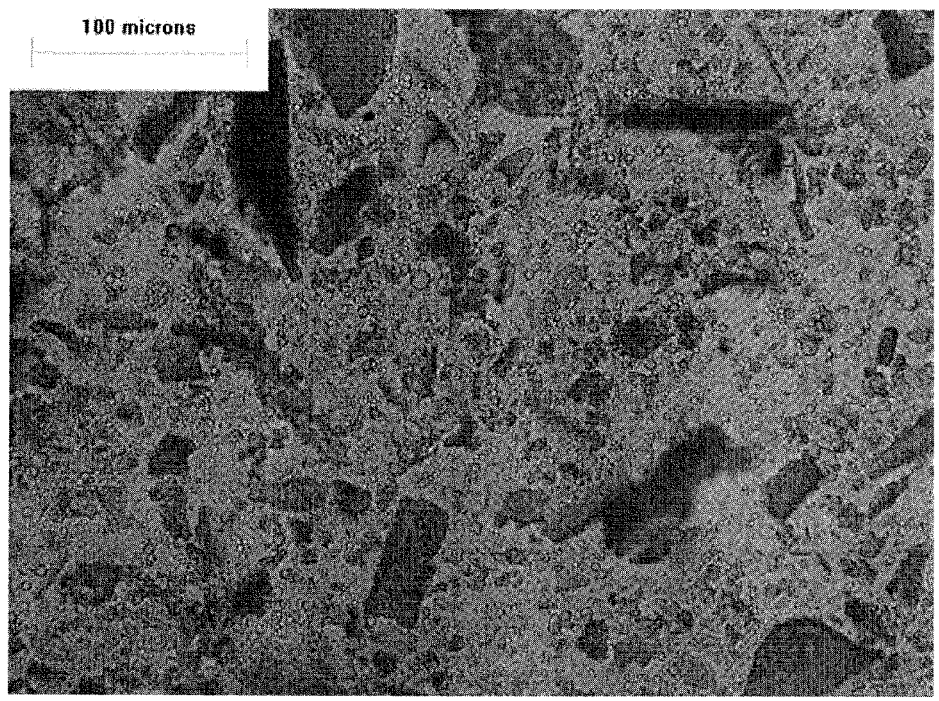
FIG. 7B is an optical microscopy of particles from Example 3.

2 g MPEG-PLGA 2-30 was dissolved in 100 ml dimethylcarbonate. To 50 mL of this solution was added 21.5 mL ethanol (EtOH). This solution was poured in an aluminium mould, and placed in the freeze dryer (shelf temperature -30° C.). When the solution was frozen, a mixture of 10 ml dimethylcarbonate and 4.3 mL EtOH is poured on top, and when this was frozen, vacuum was applied. The product was freeze dried as in example 2. The powder is characterized by optical microscopy (FIG. 7b)

Example 4

Growth of Fibroblast and Muscle Cells Together with Particles of MPEG-PLGA

Attachment and growth of fibroblasts and skeletal muscle cells on particles of MPEG-PLGA were tested in poly-HEMA coated cell culture flasks with cells and particles in suspension to prevent the cells from adhering to culture well.

Two centrifuge tubes with particles (MRG 08 095-11, Metoxy-polyethylene glycol-Poly(lactide-co-glycolide) (Mn 2,000-30,000, L:G 1:1)) were weighted and washed in 70% ethanol, centrifuged at 300 g for 7 min followed by a wash in respectively Dulbecco's Modified Eagle's Medium (DMEM) containing 10% foetal calve serum (FCS), penicillin (Pen), streptomycin (Strep) and Amphotericin B (AmpB) or F10 with 20% FCS containing Pen/Strep and human FGF. The tubes were centrifuged again in the same way as previously and dissolved in DMEM with 10% FCS and Pen/Strep/AmpB or F10 with 20% FCS pen/strep and FGF.

Primary human fibroblasts isolated from mamma reductions and primary human muscle cells isolated from muscle biopsies were cultivated in cell culture flasks. The fibroblasts and muscle cells were grown in respectively DMEM with 10% FCS and Pen/Strep/AmpB or F10 with 20% FCS pen/strep and FGF. Both cell types were at the day of the study released from the culture flasks using trypsin/EDTA.

In cell culture flasks coated with Poly (2-hydroxyethyl methacrylate) (polyHEMA, corresponding to 0.8 mg/cm$^2$), were particles and cells added to a final concentration of 1.5 mg particles/ml and $2\times10^4$ cells/ml corresponding to $1.3\times10^4$ cells/mg particles. Cell culture flasks with particles but without cells were used as controls. The flasks were cultivated at 37° C. 5% $CO_2$ for 24 hours on a shaking table at a low level and then without shaking for 4 weeks. The culture medium was replaced once a week. Evaluation of the cell attachment, morphology, growth and population of the particles were preformed at day 1 and 7 and after 2 and 4 weeks for the fibroblasts but only after 4 weeks with muscle cells. The cells were stained with neutral red followed by evaluation using a Leica DMIRE2 inverted microscope fitted with an Evolution MP cooled colour camera (Media Cybernetics). Digital images were taken using Image Pro Plus 5.1 software (Media Cybernetics).

During the first 24 hours did the fibroblasts only partly attach to the particles either as single cells on single particles or as single cells between two particles but many living cells were floating around in the media. The remaining cells in suspension were followed for the next 24-48 hours by looking at the flask using an inverted microscope and during this period were all cells attached to the particles. After 1 week were the cells attached to more particles in small clusters consisting of around 10 particles and a lot of cells and after 2 weeks were the clusters becoming even bigger and some of them seemed to grow together to even larger aggregates. Finally after 4 week only big aggregates were found (FIGS. 8A-8F).

Figure 8A:
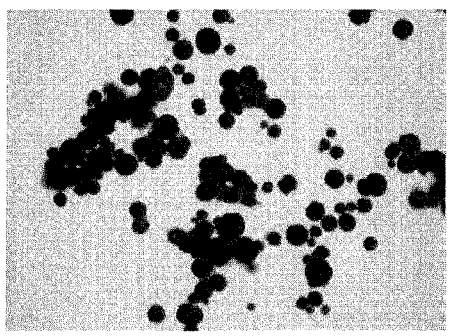
FIGS. 8A-8B show neutral red staining of fibroblasts cultivated together with particles—living cells are stained red.
  8A: 1 week—10×; 8B: 1 week—40×;
  8C: 2 weeks—10×; 8D: 2 weeks—40×;
  8E: 4 weeks—10×; 8F: 4 weeks—40×.
Figure 8B:
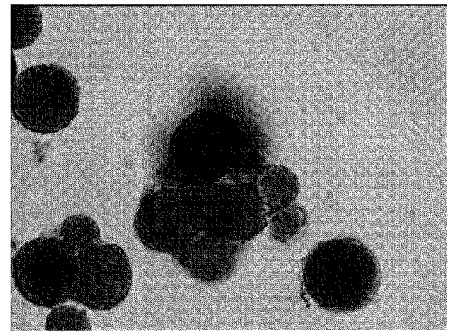
Figure 8C:
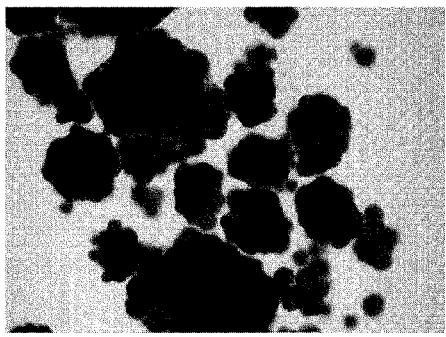
FIGS. 8G and 8H show neutral red staining of muscle cells cultivated together with particles—living cells are stained red.
  8G: 4 weeks—10×; 8H: 4 weeks—40×.
FIGS. 8J-8N show particles without cells.
  8I: Day 1—10×; 8J: Day 7—10×;
  8K: Week 2—10×; 8L: Week 2—40×;
  8M: Week 4—10×; 8N: Week 4—40×.
Figure 8D:
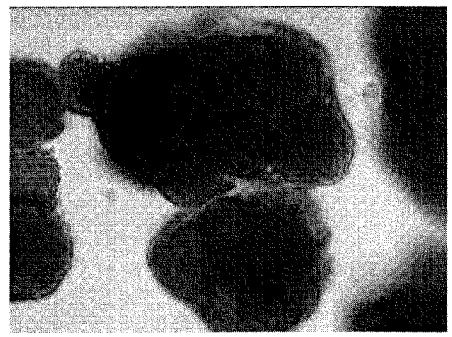
Figure 8E:
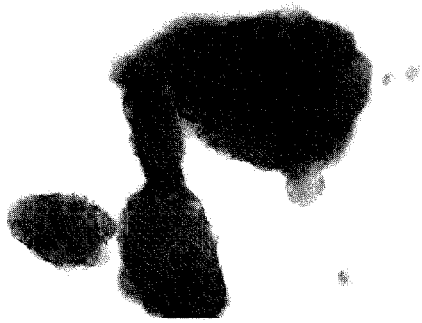
Figure 8F:
Figure 8G:
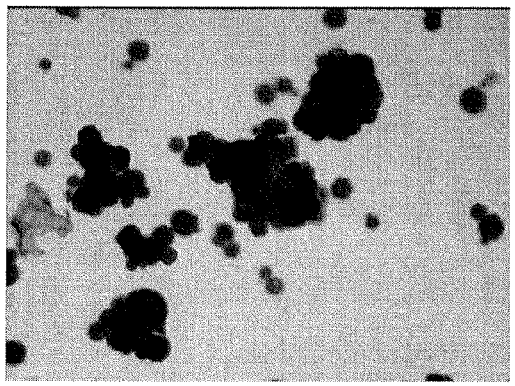
Figure 8H:
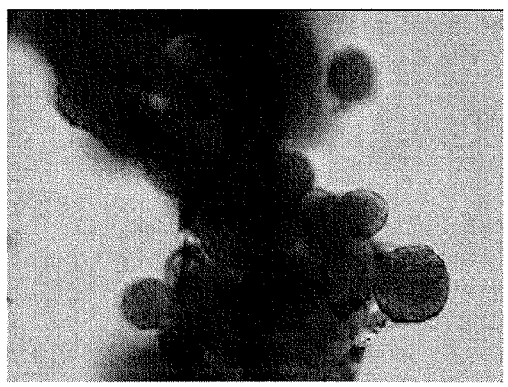
Figure 8I:
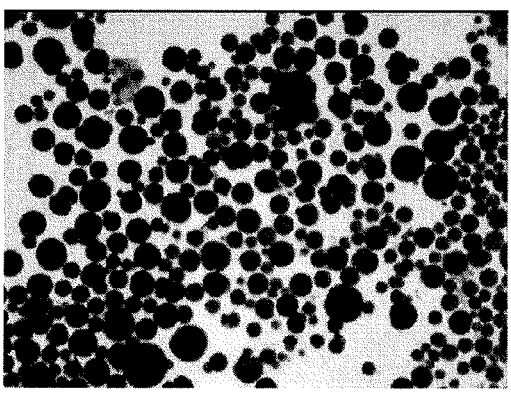
Figure 8J:
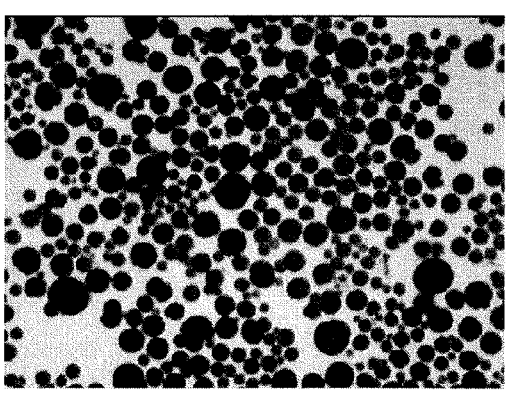
Figure 8K:
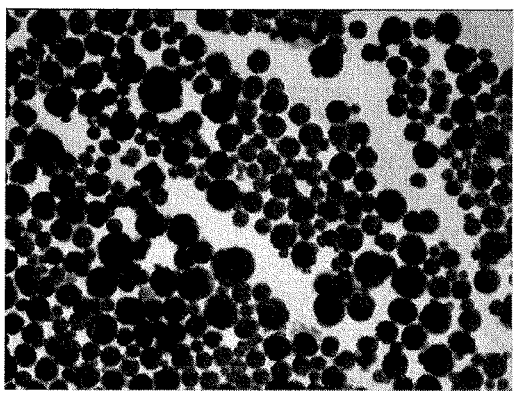
Figure 8L:
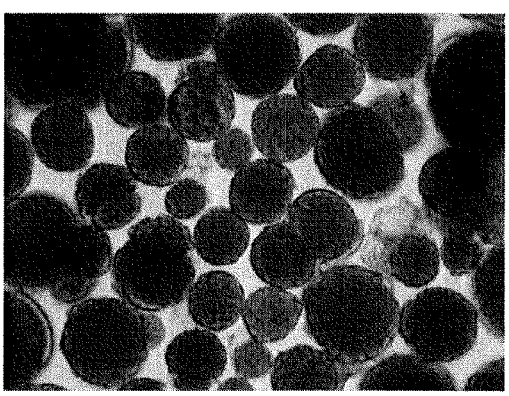
Figures 8M, 8N:
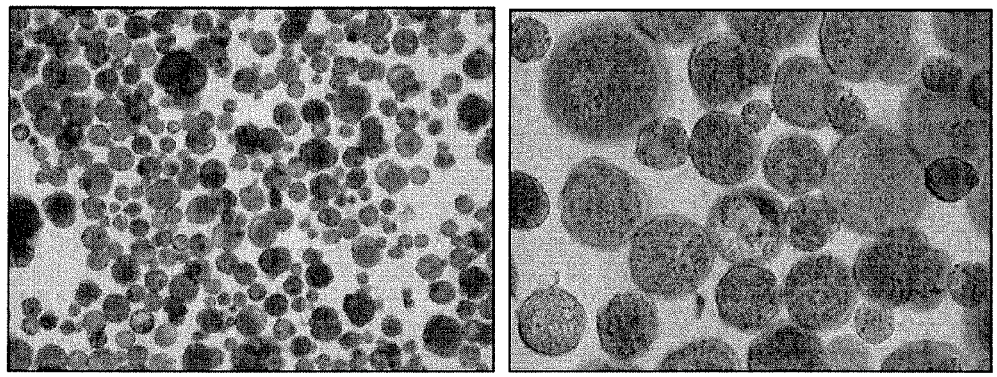
Figure 9:
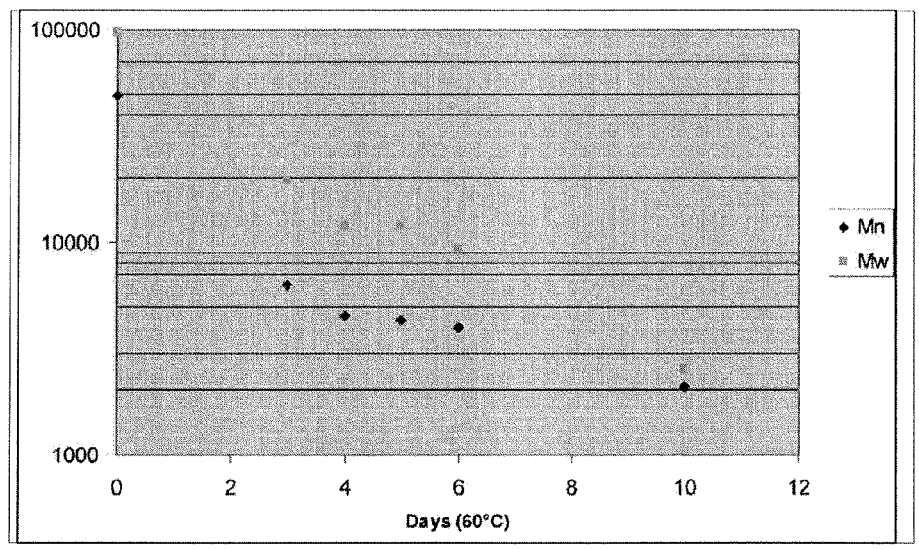
FIG. 9 graphs molecular weights of degraded samples in Example 5.

The muscle cells were only analysed after 4 weeks but here they were growing in small and large aggregates just like the fibroblasts (FIGS. 8G and 8H).

The particles that were incubated in media without cells showed during the first two weeks no apparent change in size or appearance. After 4 weeks the particles became more transparent but did not seem to become smaller. At high magnification it is possible to see that the particles are beginning to degrade with holes in the particles (FIGS. 8I-8N).

In conclusion, this study showed that both fibroblasts and muscle cells were able to attach and proliferated on the precipitated MRG 08 95-11 particles and that this resulted in large aggregates consisting of many particles hold together by many cells.

Example 5

Biodegradable MPEG-PLGA

The following method may be used to determine biodegradability of the polymer:
An accelerated degradation study of MPEG-PLGA 2-30 in phosphate buffer at 60° C. shows complete degradation after 10 days. This corresponds to 50 d at 37° C.
Materials and Methods:
Scaffolds (MPEG-PLGA 2-30 with a 50:50 DL-lactide to glycolide ratio).
12 ml screw-cap vials
GPC
Buffer: 7.4 g Na2HPO4+2.15 g KH2PO4 is dissolved in 900 mL water. pH is adjusted to 7.0 using diluted $H_3PO_4$ and volume adjusted to 1 L
Approx. 4 mg scaffold is weighed to a vial (×5), and 3 ml buffer is added. The vials are placed in an oven at 60° C. and a vial is removed at 3, 4, 5, 6 and 10 days (vials are placed in the freezer until further work).
The vials are freeze dried at -5° C. overnight, dried in a vacuum dessicator overnight, dissolved in 2 mL THF:DMF 1:1, filtered and analyzed on the GPC
Results:

| Days (60° C.) | Weight (mg) | Mn | Mw | RI area | Mn (avg) | Mw (avg) | Area (avg) | Area (norm.) |
|---|---|---|---|---|---|---|---|---|
| 0 | 5.61 | 50421 | 96460 | 16.55 | | | | 1.000 |
| 0 | | 47678 | 96218 | 18.19 | 49049 | 96339 | 17.37 | 1.099 |

| Days (60° C.) | Weight (mg) | Mn | Mw | RI area | Mn (avg) | Mw (avg) | Area (avg) | Area (norm.) |
|---|---|---|---|---|---|---|---|---|
| 3 | 4.39 | 5872 | 19190 | 13.22 | | | | 0.817 |
| 3 | | 6669 | 19769 | 12.38 | 6270 | 19479 | 12.8 | 0.765 |
| 4 | 4.43 | 4466 | 12103 | 9.5 | | | | 0.582 |
| 4 | | 4549 | 11876 | 8.99 | 4507 | 11989 | 9.245 | 0.550 |
| 5 | 4.13 | 4388 | 11902 | 8.02 | | | | 0.527 |
| 5 | | 4274 | 11965 | 7.79 | 4331 | 11933 | 7.905 | 0.511 |
| 6 | 3.87 | 3517 | 8875 | 5.21 | | | | 0.365 |
| 6 | | 4460 | 9609 | 4.16 | 3988 | 9242 | 4.685 | 0.291 |
| 10 | 4.67 | 1973 | 2477 | 1.16 | | | | 0.067 |
| 10 | | 2184 | 2512 | 0.71 | 2078 | 2494 | 0.935 | 0.041 |

Figure 10:
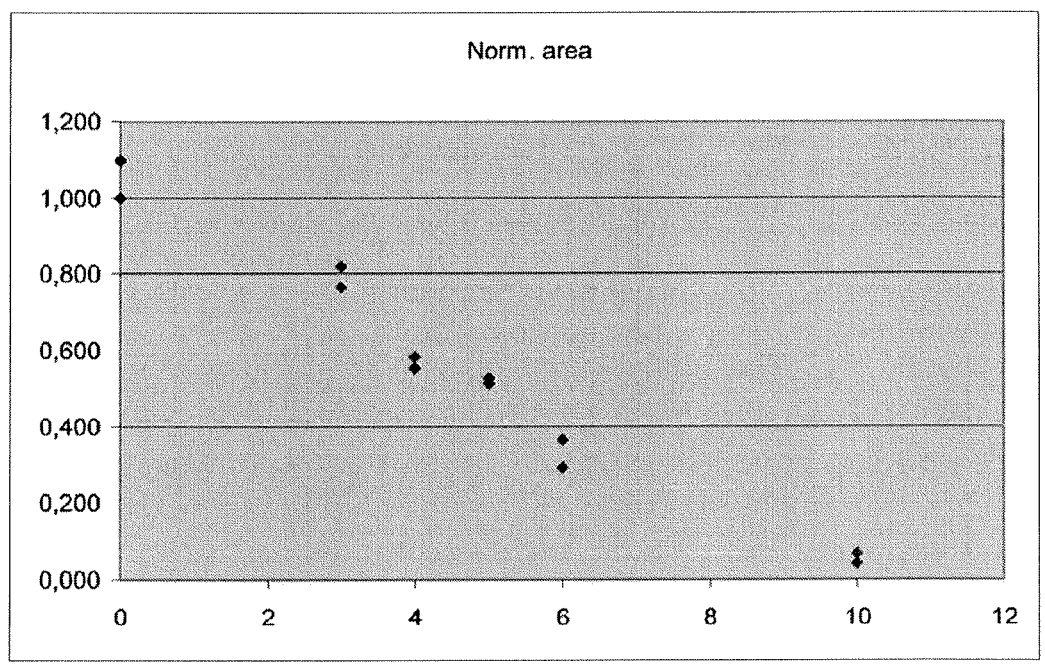
FIG. 10 graphs normalized area of degraded samples in Example 5.
Figures 12A, 12B, 12C:
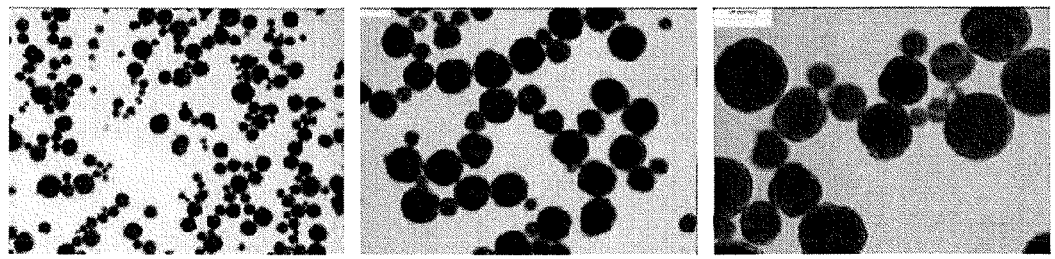
Figures 12D, 12E:
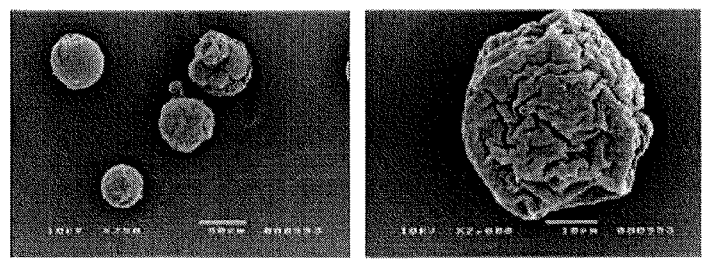
Figure 12F:
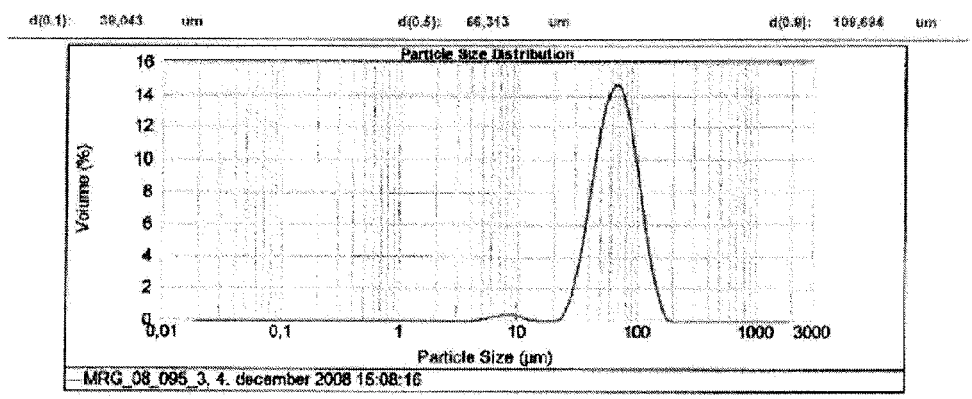
Figure 16A:
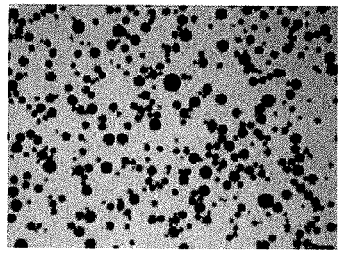
Figure 16B:
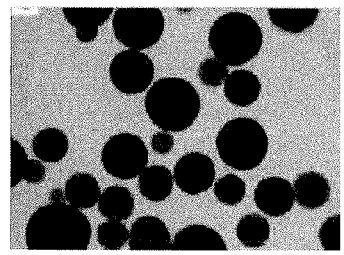
Figure 16C:
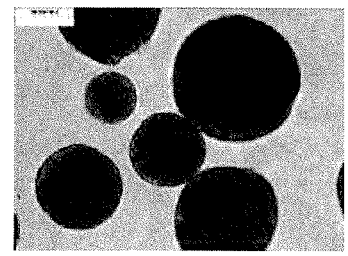
Figure 16D:
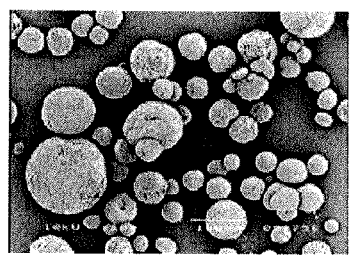
Figure 16E:
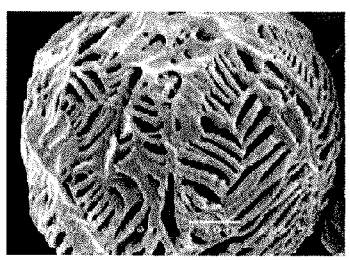
Figure 16F:
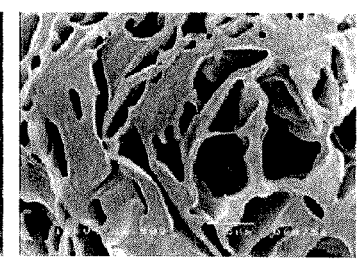
Figure 16G:
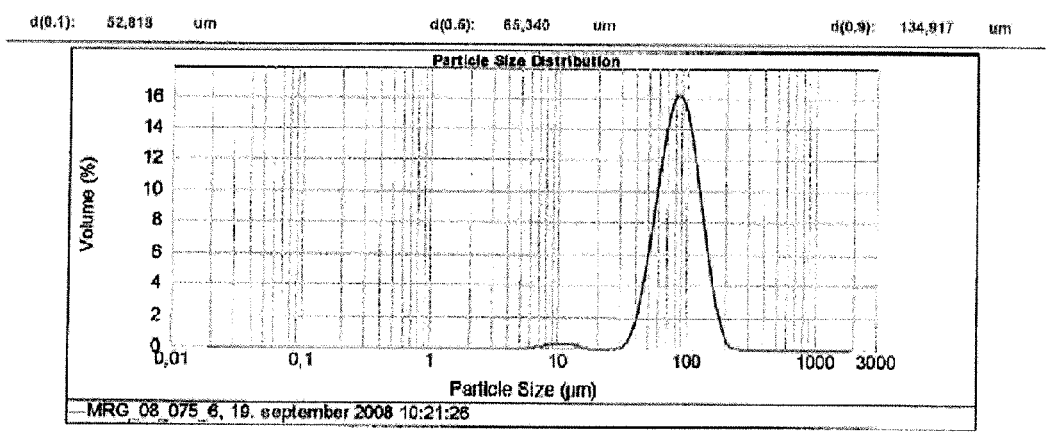

After 10 days, complete degradation is seen, and the only peak remaining in the chromatogram is MPEG. This would correspond to approximately 50 days at 37° C. See FIGS. 9 and 10.

Example 6

Chondrocytes Mixed with MPEG-PLGA Microparticles

Human articular chondrocytes (hACs, passage 1) are cultured in DMEM-12 containing 16% fetal bovine serum (FBS), ascorbic acid (75 μg/ml), fungizone (2.4 μg/ml) and gentamicin (10 mg/ml), together with MPEG-PLGA microparticles (1.5 mg/ml) as prepared in the previous examples.

hACs are cultured together with the microparticles for 14 days in an atmosphere of 5% $CO_2$ at a temperature of 37° C.

After 14 days in culture, microparticles coated with hACs were divided into to samples. One sample were stained with Neutral Red (Sigma-Aldrich), in order to visualize the attachment of chondrocytes to the microparticles and the other sample were embedded in Tissue-Tek (Sigma-Aldrich) and sectioned in a cryostat at −26 degrees with a thickness of 10 μm. Sections were stained with 0.5% Toluidine Blue (Sigma-Aldrich) in order to visualize the synthesis of ECM proteins in the samples.

Figure 23:
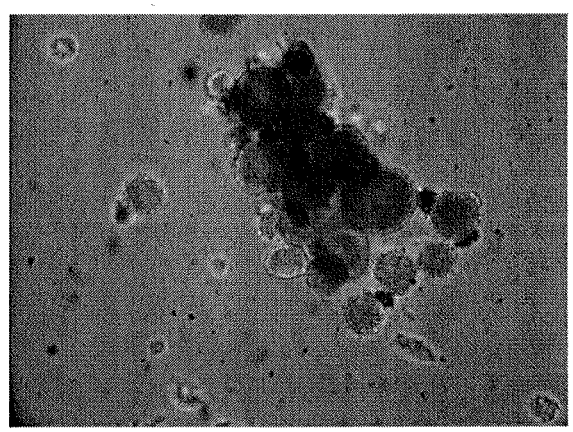
FIG. 23 shows hACs (red color) attached to MPEG-PLGA microspheres after 14 days in culture.
Figure 24:
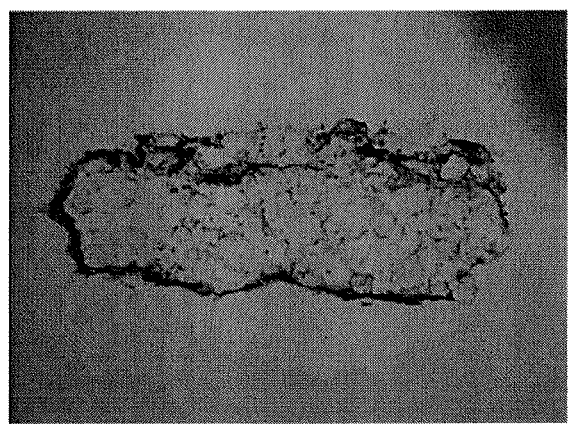
FIG. 24 shows ECM synthesis (blue color) by hACs on MPEG-PLGA microspheres after 14 days in culture.

On FIGS. 23 and 24 it is demonstrated that combining hACs with MPEG-PLGA microparticles, results in the attachment of hACs to the microparticles and that the attached hACs is able to produce a extracellular matrix on—and within the particles.

Example 7

Ultrasonic Atomisation-Precipitation

General Equipment

The experiments described below were conducted by using a 20 kHz probe from Sonics and a 25 kHz conical probe from Sonotek. The flying distance of the atomized polymer was 40-50 cm before it hit its collection reservoir in a chamber kept at −70° C. The temperature inside the receiving chamber and in the collection reservoir was controlled using a refrigerated system.

General Procedure 10, 7.5 and 5% (w/v) 2-30 MPEG-PLGA polymer solutions in acetone or in acetone in combination with a non-solvent such as ethanol or hexane, were atomised by an ultrasonic probe into a −70° C. chamber and received into a bath of isopropanol at −65° C. to −70° C. The suspension of the particles was filtered by suction or decanted and the particles were then dried under vacuum and stored cold in airtight close vials.

Experimental parameters included are presented in Table below

| Experiment No. | Polymer concentration % (w/v) | Non-solvent 9% (v/v) | Ultrasonic atomizer (kHz) | Characterization FIG. No. |
|---|---|---|---|---|
| 7 | 5 | None | 25 | 11A-11G |
| 8 | 7.5 | None | 25 | 12A-12F |
| 9 | 7.5 | EtOH | 25 | 13A-13F |
| 10 | 10 | EtOH | 25 | 14A-14L |
| 11 | 7.5 | Hexane | 25 | 15A-15F |

Example 8

Ultrasonic Atomisation-Freeze Drying

General Procedure 10, 7.5 and 5% (w/v) 2-30 MPEG-PLGA polymer solutions in dimethylcarbonate (DMC) or dioxane or combination of DMC and dioxane were atomised by an ultrasonic probe into a −70° C. chamber and received into aluminium trays kept at the same temperature. The trays containing the spray were transferred to a freeze dryer at −20° C. and dried overnight. The particles were then transferred to a desecator, for further drying under vacuum and stored cold in airtight close vials.

Experimental parameters included are presented in Table below

| Experiment No. | Solvent | Polymer concentration (% w/v) | Ultrasonic Atomizer (kHz) | Characterization shown in FIG. |
|---|---|---|---|---|
| 12 | DMC | 10 | 25 | 16 |
| 13 | DMC | 10 | 20 | 17 |
| 14 | DMC | 7.5 | 25 | 18 |
| 15 | DMC | 5 | 25 | 19 |
| 16 | Dioxane | 7.5 | 25 | 20 |
| 17 | Dioxane | 10 | 25 | 21 |
| 18 | Dioxane:DMC (1:1) | 7.5 | 25 | 22 |

Example 9

Characterization of the Microparticles by Bulk Density Measurements

Particles were collected into an enclosed container containing a plunger and volumetric graduation. The particles were pressed by applying a slow compressive force in the range of 1-2.5 $N/mm^2$.

The weight and volume occupied by the particles was recorded.

Data obtained for selected samples is presented in Table below

| Experiment No | Bulk Density (g/ml) |
|---|---|
| 3 | 0.24 |
| 10 | 0.29 |
| 12 | 0.13 |
| 13 | 0.15 |
| 14 | 0.12 |

The invention claimed is:

1. A method for treating incontinence comprising regeneration or augmentation of sphincter muscle tissue in a patient by the steps of
obtaining a composition comprising a population of porous microparticles of biodegradable polymer and a population of myoblasts in the absence of a biocompatible adhesive and
administering the composition to sphincter muscle tissue of a patient in need thereof.

2. The method according to claim 1, wherein administering the composition is by injection.

3. The method according to claim 1, wherein the porous microparticles have a porosity of 50 to 95%.

4. The method according to claim 1, wherein the porous microparticles have a size of 20-110 μm.

5. The method according to claim 1, wherein the composition further comprises one or more mammalian cell populations.

6. The composition according to claim 1, wherein the composition further comprises one or more mammalian cell populations attached to the population of porous microparticles.

7. The method according to claim 1, wherein the porous microparticles are microspheres.

8. The method according to claim 1, wherein the porous microparticles have irregular shapes.

9. The method according to claim 1, wherein the porous microparticles are flake shaped.

10. The method according to claim 1, wherein the biodegradable polymer is selected from the group consisting of
a) homopolymers and copolymers of glycolide,
b) block-copolymers of mono- and difunctional polyethylene glycol and (a),
c) block copolymers of mono- and difunctional polyalkylene glycol and (a),
d) blends of (a), (b), and (c), and
e) polyanhydrides and polyorthoesters.

11. The method according to claim 1, wherein the biodegradable polymer is selected from the group consisting of
a) homopolymers and copolymers of L-lactide, DL-lactide, meso-lactide (polylactide, PLA), e-caprolactone (polycapro-lactone, PCL), 1,4-dioxane-2-one, d-valerolactone, β-butyrolactone, e-butyrolactone, e-decalactone, 1,4-dioxepane-2-one, 1,5-dioxepan-2-one, 1,5,8,12-tetraoxacyclotetradecane-7-14-dione, 1,5-dioxepane-2-one, 6,6-dimethyl-1,4-dioxane-2-one, and trimethylene carbonate,
b) block-copolymers of mono- and difunctional polyethylene glycol and (a),
c) block copolymers of mono- and difunctional polyalkylene glycol and (a),
d) blends of (a), (b), and (c), and
e) copolymers of poly(D,L-lactide-co-glycolide) (PLGA) and (methoxypolyethyleneglycol)-poly(D,L-lactide-co-glycolide) (MPEG-PLGA).

12. The method according to claim 1, wherein the biodegradable polymer is PLGA or MPEG-PLGA.

13. The method according to claim 1, wherein the porous microparticles are prepared by freeze drying a solution comprising the biodegradable polymer.

14. The method according to claim 1, wherein the microparticles are prepared by ultrasonic atomisation.

15. The method according to claim 1, wherein the composition further comprises one or more mammalian cell populations, wherein the cells are autologous, homologous (allogenic), or xenogenic in origin relative to cells of the patient.

16. The method according to claim 1, wherein the composition further comprises one or more mammalian cell populations, wherein the cells are autologous, homologous (allogenic), or xenogenic in origin relative to cells of the patient, and wherein the cells are present in the composition at a concentration of about $0.1 \times 10^4$ cells per ml to about $10 \times 10^6$ cells per ml.

17. The method according to claim 1, wherein the composition further comprises a component facilitating cell in-growth for regeneration of tissue to the porous microparticles.

18. The method according to claim 1, wherein at least some of the porous microparticles incorporate a compound selected from the group consisting of hydroxyapatite, calcium phosphate, and a combination thereof.

* * * * *